United States Patent
Adar et al.

(10) Patent No.: US 10,015,952 B2
(45) Date of Patent: Jul. 10, 2018

(54) SYSTEM AND METHOD FOR MONITORING EGGS DURING INCUBATION

(71) Applicant: LIVEGG (2015) LTD, Ma'anit (IL)

(72) Inventors: Gavriel Adar, Kvutzat Yavne (IL); Eliyahu Hoffman, Jerusalem (IL); Yair Or Adar, Kvutzat Yavne (IL)

(73) Assignee: LIVEGG (2015) LTD., Ma'anit (IL)

(*) Notice: Subject to any disclaimer, the term of this patent is extended or adjusted under 35 U.S.C. 154(b) by 109 days.

(21) Appl. No.: 14/967,944

(22) Filed: Dec. 14, 2015

(65) Prior Publication Data

US 2016/0100557 A1   Apr. 14, 2016

Related U.S. Application Data

(63) Continuation-in-part of application No. PCT/IB2014/065066, filed on Oct. 5, 2014.

(30) Foreign Application Priority Data

Oct. 7, 2013 (GB) .................................. 1317653.2

(51) Int. Cl.
  *A01K 29/00* (2006.01)
  *A01K 41/00* (2006.01)
  (Continued)

(52) U.S. Cl.
  CPC ............ *A01K 41/00* (2013.01); *A01K 29/005* (2013.01); *A01K 43/00* (2013.01); *G01N 21/47* (2013.01);
  (Continued)

(58) Field of Classification Search
  CPC ...... A01K 41/00; A01K 29/005; A01K 43/00; A01K 41/065; A01K 43/04; G01N 21/47; G01N 21/474; G01N 33/085; H04W 84/12
  (Continued)

(56) References Cited

U.S. PATENT DOCUMENTS 3,147,738 A * 9/1964 Theilig .................. A01K 41/06
119/322
3,540,824 A * 11/1970 Fonda .................... G01N 33/08
209/3.3
(Continued)

FOREIGN PATENT DOCUMENTS

EP    0 715 168       6/1996
FR    2755580 A1      5/1998
(Continued)

OTHER PUBLICATIONS

GB Search Report, dated Jan. 28, 2014. In corresponding application No. GB1317653.2.
(Continued)

*Primary Examiner* — Monica L Williams
*Assistant Examiner* — Brady W Frazier
(74) *Attorney, Agent, or Firm* — Browdy and Neimark, P.L.L.C.

(57) ABSTRACT

An incubation tray is disclosed, including an enclosure with a plurality of egg placements for carrying eggs for incubation within an egg incubator. The incubation tray includes a tester unit including plurality of inspection modules in the enclosure associated with the plurality of egg placements. The inspection modules, each includes radiation emitter(s) and sensor(s), and are configured and operable for respectively inspecting the plurality of eggs located in the egg placements, by irradiating the eggs with radiation from a lateral side of the eggs and measuring a radiation response coming in response to the irradiation from a lateral side of the eggs, giving rise to measured data indicative of conditions of the eggs. The measured data may be processed to determine dynamic and static parameters of the radiation response from which a physiological development stage, and growth of the embryos within the eggs can be estimated.

27 Claims, 19 Drawing Sheets

(51) Int. Cl.
*A01K 43/00* (2006.01)
*G01N 33/08* (2006.01)
*G01N 21/47* (2006.01)
*H04W 84/12* (2009.01)
*G01N 21/01* (2006.01)

(52) U.S. Cl.
CPC ......... *G01N 21/474* (2013.01); *G01N 33/085* (2013.01); *H04W 84/12* (2013.01); *G01N 2021/0112* (2013.01); *G01N 2201/062* (2013.01); *G01N 2201/06113* (2013.01)

(58) Field of Classification Search
USPC ........................................................ 119/322
See application file for complete search history.

(56) References Cited

U.S. PATENT DOCUMENTS

| | | | | |
|---|---|---|---|---|
| 4,164,291 A | * | 8/1979 | Carlow | B07C 5/361 198/349.95 |
| 4,955,728 A | | 9/1990 | Hebrank | |
| 5,173,737 A | * | 12/1992 | Mitchell | A01K 45/00 356/53 |
| 5,745,228 A | | 4/1998 | Hebrank et al. | |
| 5,898,488 A | * | 4/1999 | Kuhl | A01K 43/00 356/53 |
| 6,373,560 B1 | * | 4/2002 | Roux | G01N 21/15 209/510 |
| 6,427,844 B2 | * | 8/2002 | Hebrank | A01K 43/00 209/510 |
| 6,488,156 B1 | * | 12/2002 | Cohen | A01K 43/00 209/510 |
| 6,535,277 B2 | * | 3/2003 | Chalker, II | A01K 43/00 356/52 |
| 7,041,439 B2 | * | 5/2006 | Phelps | A01K 45/00 119/6.8 |
| 7,333,187 B2 | | 2/2008 | Hebrank | |
| 7,430,987 B2 | * | 10/2008 | Smith | A01K 45/007 119/6.8 |
| 8,724,098 B2 | * | 5/2014 | Adjanohoun | G01N 33/085 356/53 |
| 2002/0014444 A1 | | 2/2002 | Hebrank | |
| 2004/0107912 A1 | * | 6/2004 | Hebrank | A01K 43/00 119/6.8 |
| 2005/0174824 A1 | | 8/2005 | Reeves et al. | |
| 2005/0206876 A1 | * | 9/2005 | Reeves | A01K 43/00 356/52 |
| 2006/0082759 A1 | | 4/2006 | Hebrank | |
| 2007/0024843 A1 | | 2/2007 | Hebrank et al. | |
| 2009/0091742 A1 | | 4/2009 | Hebrank et al. | |
| 2010/0141933 A1 | * | 6/2010 | Nadreau | A01K 43/00 356/53 |
| 2011/0141455 A1 | | 6/2011 | Adjanohoun | |

FOREIGN PATENT DOCUMENTS

GB 2166333 A 5/1986
WO 2015145435 A1 10/2015

OTHER PUBLICATIONS

International Search Report, dated Dec. 28, 2014. In corresponding application No. PCT/IB2014/063066.

* cited by examiner

SYSTEM AND METHOD FOR MONITORING
EGGS DURING INCUBATION

CROSS-REFERENCE TO RELATED
APPLICATIONS

The present application is a continuation-in-part of PCT/IB2014/065066, filed Oct. 5, 2014, which claims priority to British application 1317653.2, filed Oct. 7, 2013, both of which are hereby incorporated by reference herein.

BACKGROUND

Technical Field

The present invention relates to incubation and hatching of eggs such as poultry eggs for breeding, and in particular to a system and method for determining the fertility and viability of the eggs.

Description of Related Art

Fertile eggs contain a living cell mass that develops into an embryo, and finally into a hatchling, e.g. a chick. After eggs have been selected or acquired for incubation, care is required to prevent damage or contamination of the eggs.

Eggs are set in incubator trays in movable trolleys and placed in an incubator. Temperature, humidity and oxygen levels of the incubators are controlled so that the incubators have a stable environment, free of drafts and away from direct sunlight.

Eggs may be inspected by conventional candling to determine viability during incubation. Candling may be performed by removing an egg trolley from the incubator and entering a dark room suitable for candling. A light source is then used to manually inspect a sample of the eggs for viability, typically one egg at a time. A small reddish area with blood vessels extending away from it is visible in fertile eggs. The small reddish area is the embryo floating inside the egg. If the embryo dies, the blood draws away from the embryo and forms what is called a blood ring. All clear eggs and eggs showing blood rings or streaks are removed from the incubator. If egg samples are not candled during the early stages of incubation, it will be difficult to determine whether the eggs are originally infertile or whether there is a problem with the incubation conditions in the incubator.

At best, about ninety percent of incubated eggs are expected to yield healthy hatchlings. Embryo death of originally fertile eggs may occur during different periods of incubation. Some eggs are classified as "early dead" when the embryo dies during the first quarter period of incubation, as "middle dead" when the embryo dies before transfer to the hatchery, or as "late dead" when the embryo dies during the last few days immediately before a hatch. Embryo death may lead to eggs exploding during the hatching stage. These eggs are called "black eggs" and may contaminate other eggs and/or hatchlings, causing considerable financial loss.

Thus there is a need for and it would be advantageous to have a system and method for a system for determining viability of a sample of eggs during incubation in the incubator while avoiding transporting the eggs to a dark room for candling and avoiding contact with the eggs. Moreover, it would be advantageous to have a system and method for determining the viability of eggs to enable subsequent transfer of viable eggs to a hatching tray while leaving non-viable eggs in the original incubation tray. Moreover, it would be advantageous to have a system and method for monitoring embryo development during incubation and optionally for controlling incubation parameters according to monitored development.

BRIEF SUMMARY

Various computerized systems are provided herein, adapted for simultaneously determining viability of multiple eggs in an incubation tray. A tester unit including an arrangement of a plurality of inspection modules for inspecting a plurality of eggs is provided. The tester unit is operable to simultaneously determine the locations within the incubation tray of the viable eggs or of the non-viable eggs. The tester unit includes, or is associated with a processing system (hereinafter also referred to as a processor), which is configured and operable for processing the measured data obtained from the tester unit to determine the condition of the eggs examined by the tester unit. The tester unit includes multiple compartments (hereinafter also referred to as housings) accommodating the plurality of inspection modules and defining egg placements at which the eggs can be placed and inspected by the inspection modules respectively. Each of the inspection modules includes a source/emitter emitting radiation and a corresponding sensor for measuring the radiation scattered (reflected/transmitted) from the egg in response to the radiation directed thereto by the emitter, which is hereinafter referred to also as radiation response. During operation of the system, the sources are configured to emit radiation towards the eggs (e.g. into the interior of the eggs) and the respective sensors sense a portion of the radiation response that is scattered from the eggs (e.g. from the interior of the eggs) and returns from or is transferred through the eggs. The signals measured from the sensors of the inspection modules are recorded/stored (e.g. in a storage module of the tester unit) to provide measured data indicative of the condition/viability of the eggs according to their locations.

Thus, according to a broad aspect of the present invention there is provided an incubation tray that is adapted for placement within an egg incubator and includes an enclosure defining a plurality of egg placements for carrying a plurality of eggs for incubation within an egg incubator. The incubation tray includes a tester unit comprising a plurality of inspection modules located by the enclosure and associated with the plurality of egg placements respectively. The inspection modules, each includes at least one radiation emitter and at least one sensor, and are configured and operable for respectively inspecting the plurality of eggs located in the egg placements, by irradiating the eggs with radiation from a lateral side of the eggs and measuring a response from a lateral side of the eggs to determine measured data indicative of conditions of the eggs in the egg placements. The incubation tray of claim 1 wherein the condition of the eggs is indicative of at least one of the following: condition of embryos within the eggs and condition of shells of the eggs.

According to another broad aspect of the present invention there is provided an incubation tray including at least one tilt sensor capable of measuring tilting of eggs in the incubation tray. The incubation tray also includes a controller, connectable to the tilt sensor for receiving therefrom measured tilt data indicative of the tilting, and a communication module, associated with the controller. The communication module is adapted for communicating the measured tilt data to a processing system to enable processing the measured tilt data to determine the incubation condition applied to the eggs based on the measured tilt data.

According to yet another broad aspect of the present invention there is provided a processing system for processing measured data of radiation response from an egg. The processing system includes:

- a communication module for obtaining measured data indicative of radiation response obtained by irradiating an egg for a duration of at least a few seconds and detecting the radiation scattered from the egg at the duration;
- a dynamic parameter analyzer adapted to process the measured data to determine dynamic parameters indicative of periodical variations in the intensity of the radiation response from the egg and utilize the dynamic parameters to estimate physiological development stage of an embryo within the egg;
- a static parameter analyzer adapted to process the measured data to determine static parameters indicative of a magnitude of the radiation response from the egg and utilize the static parameters to estimate growth of the embryo within the egg; and
- an embryo condition estimator configured to determine a condition of the embryo based on the estimated growth and the physiological development stage of the embryo.

According to yet further broad aspect of the present invention there is provided a method for processing measured data indicative of radiation response obtained from an egg. The method includes:

- obtaining measured data indicative of radiation response from an egg during a one or more inspection sessions, each including irradiating the egg by radiation for a duration of at least a few seconds, and detecting radiation response indicative of radiation scattered from the egg at the duration;
- processing the measured data from the one or more inspection sessions to determine dynamic parameters indicative of periodical variations in the intensity of the radiation response from the egg and utilize the dynamic parameters to estimate physiological development stage of an embryo within the egg;
- processing the measured data to determine static parameters indicative of a magnitude of the radiation response from the egg and utilizing the static parameters to estimate a size of the embryo within the egg; and
- estimating a condition of the embryo based on the estimated size of the embryo, and physiological development stage of the embryo.

According to some embodiments of the present invention the one or more inspection sessions include at least two inspection sessions. The method includes utilizing the static parameters to determine sizes of the embryo in the inspection sessions and thereby determine a growth of the embryo in between the inspection sessions, and wherein the growth is indicative of a condition of the embryo.

In some implementations of the tester unit of the invention, the radiation emitted by the emitter and detected by the sensor may be electromagnetic (EM) radiation, such as optical radiation/light in the infrared (IR) regime (e.g. in the Near IR) and/or radio frequency radiation (RF waves). Alternatively or additionally, in some embodiments the radiation emitted by the emitter and detected by the sensor may be acoustic radiation (acoustic waves), such as ultrasound waves.

In cases where the invention is implemented using radiation/light in the IR or Near IR regime, the emitter and sensor are configured and operable in this regime. The emitter may be a source of optical/IR radiation, such as a laser or a light emitting diode (LED) operative to emit EM radiation in this regime or a wave guide (such as an optical fiber) connected to such a source. The sensor may be a photo detector operative in this regime. The signals detected/measured by the sensor, indicative of scattered radiation from the interior of the egg (e.g. from the embryo), may be processed to determine the size/growth of the embryo and/or its physiological development stage.

In cases where the invention is implemented using radiation/light in the RF regime, the tester unit may be configured to operate according to Nuclear Magnetic Resonance (NMR) or Magnetic Resonance Imaging (MRI) principles. In this case the emitter of the inspection module (which may be an antenna associated with an RF transmitter) is configured to emit RF radiation (radio wave energy) for instance in pulses, towards an egg in an egg/incubation tray, while the eggs are under the influence of a strong magnetic field (which can be applied by utilizing a strong magnetic field source that may be for example located in the incubator). The sensor, which may be an antenna (e.g. the same one as the emitter, or a different one associated with a receiver) is operated to detect the electromagnetic field associated with the magnetic resonance caused by the combination of the magnetic field and transmitted RF signal. Measured data on magnetic resonance of the material of the eggs is further processed according to conventional MRI or NMR techniques and used to determine data indicative of the condition of the egg/embryo thereinside.

In cases where the invention is implemented using acoustic radiation (acoustic waves), such as ultrasound waves, the emitter and sensor are configured and operable as acoustic transducers (possibly directional acoustic transducers such as phased array transducers) capable of respectively emitting and directing acoustic radiation (waves) e.g. focused to various regions in the egg, and receiving acoustic responses from the egg corresponding to the scattering/reflection/refraction of the acoustic waves from the egg. Optionally one or both of the acoustic transducers of the emitter and/or sensors are configured and operable as directional transducers operable to emit/receive acoustic radiation from particular controllable directions. In this case the tester unit may be adapted to perform acoustic scanning such as ultrasound scanning to obtain measured data indicative of the content of the egg (e.g. the embryo thereinside) or to obtain measured data indicative of the integrity of the egg shell (e.g. indicative of existence of cracks/breaks in the egg shell).

In some implementations the tester unit is a standalone unit configured to be locatable entirely above and/or entirely below the incubation tray in close proximity to eggs in the incubation tray while avoiding contact with the eggs. Inspection is performed by detecting the radiation response scattered from interior of the egg and returning to the sensors (which are located at the same side of the emitter. In this case, inspection of the eggs is performed along a vertical axis, with illumination and detection paths being from above or below the eggs generally along the longitudinal axis of the eggs (which is about parallel to the vertical axis when the eggs are in the tray). The incubation tray may be situated in a setting room and the testing is performed in the setting room. In preparation for transfer to a hatching tray, the tester unit may be (re)located outside the setting room where the testing is performed, and a removal mechanism may be subsequently located above the incubation tray.

In some implementations, the tester unit (namely the inspection modules thereof) is integral with the incubation tray, and may be used for testing the condition/viability of the eggs when they are located on the tray within the egg incubator. In such implementations inspection of the eggs may be performed by measuring the radiation response scattered from the interior of the egg and transferred-through or returning back from, the egg. In this case, where the tester unit is integral with the tray, the emitter and the sensor (also referred to herein as detector) may be located at the side walls of the tray, such that the illumination and detection paths are substantially along the horizontal plane. In this case, inspection of the eggs is performed from a lateral/transverse plane of the egg.

The measured data, from the tester unit may be used/processed to determine the locations of non-viable eggs or eggs whose condition is poor (not suited for further incubation or hatching), within the incubation tray, thus allowing transfer of poor condition eggs out from the incubation tray.

Alternatively or additionally, based on the locations, simultaneous transfer of the viable eggs may be enabled from the incubation tray to a hatching tray while leaving the non-viable eggs in the incubation tray.

A conveyor may be used to convey the incubation tray from a first position (e.g. being within the eggs incubator or the setting room where testing the egg conditions is performed), to a second position below the removal mechanism, where removal of poor condition eggs and/or viable/good condition eggs is performed.

The controller(s) of inspection modules is connectable to the electromagnetic sensors of the inspection modules and is configured and operable to receive therefrom, in real-time, signals from the electromagnetic sensors, and to utilize the signals to store measured data indicative of the condition/viability of the eggs according to their locations.

The processor is programmed to communicate with the controller(s) of the inspection modules (via wireless or wired communication) to obtain the measured data and process/analyze the measured data to determine thereby the conditions of the eggs in the respective locations in the tray (e.g. to determine which of the eggs are viable). This may be achieved by measuring amount/intensity of radiation scattered from the egg (e.g. analyzing the transmittance through the egg by measuring the DC component of the radiation response from the egg) and utilizing it to estimate the size/age of the embryo in the egg and and/or its development stage. Alternatively or additionally, this can be achieved my measuring dynamic parameters (AC components) of the radiation response from the egg (e.g. by identifying the timing of appearance of periodic changes in the scattering occurring with frequencies corresponding to existence/appearance of heartbeat of the embryo (e.g. at about day 17) or with existence/appearance low frequency variations in the radiation response (e.g. at about day 7) which may be attributed to the breathing cycle of the embryo). The latter case, in which the AC component is analyzed, may be performed, for instance, in accordance with the technique for examining eggs disclosed in PCT patent publication no. WO2015145435, or by any other technique that is suited for processing/analyzing measured data on the radiation response from the egg during incubation. To this end the processor may be adapted for obtaining from the controller(s) measured data corresponding to the radiation response from the eggs acquired at one or more inspection sessions (one or more time intervals) during the incubation period, analyzing the measured data to determine the conditions of the eggs, for instance based on the intensity of the radiation response from each egg, and/or by identifying predetermined dynamics in intensity variations of the radiation response during the different time intervals (measurement/inspection sessions). Accordingly, the processor may be adapted to identify, during one or more inspection sessions, the presence of an alive embryo in each egg (namely to determine whether the egg is viable), and possibly also determine other parameters associated with the condition of the egg, such as the development stages and age of the embryo being developed therein. The processor stores data on the condition/viability of the eggs (e.g. viable eggs or non-viable eggs) and their positions in the incubation tray, in a memory/storage module associated therewith.

The controller(s) of inspection modules is connectable to the emitters (e.g. sources/wave-guides) of radiation of the inspection modules, for example via a multiplexer. The multiplexer may be operatively connected to the controller. Under control of the controller, the multiplexer signals the sources of radiation to emit radiation during predetermined time slots. The signals may be synchronized with the time slots to reduce cross-talk between the signals.

Memory of the processor, which is used to store the data on the condition of eggs, may be accessible by the removal mechanism. The memory is configured to store the locations in the incubation tray of the viable eggs, or of the non-viable eggs.

In implementations of the tester units, in which the inspection modules are configured to perform inspection from one side of the egg (namely to illuminate and detect the radiation response from the seam side), the emitter and detector of the inspection modules are located such that the scattering angle between the center of emission from the sources of radiation and the center of reception of the respective electromagnetic sensors (namely the angle between the illumination and detection optical paths) is between 50 and 120 degrees. This provides for reducing the detection of reflections of the illuminating radiation from the egg shell, and thereby improves the accuracy and reliability of the measurements of the intensity of the radiation response scattered from within the egg.

In some implementations, particularly when the tester unit is a standalone unit configured for being located above or below the incubation tray, the distance between the housings/compartments of the tester unit (at which the emitters and sensors of the inspection modules are located) and the respective eggs may be between 1 and 15 millimeters.

The emitters/sources may be configured to emit radiation into the interior of the eggs and the respective sensors may sense a portion of the radiation scattered from the interior of the eggs. The controller(s) may be operatively attached to the sensors and may receive therefrom, in real-time, signals indicative of the radiation response from the eggs, and store the measured data. The processor may be programmed to communicate with the controllers to obtain and process the measured data to determine thereby which of the eggs are viable and store the locations in the incubation tray of the viable eggs or of the non-viable eggs. A change in the signals may indicate movement of a live embryo within the viable eggs, breathing cycles, or a heartbeat of a live embryo in the viable eggs and/or hemoglobin in the viable eggs being oxygenated.

Various computerized methods for simultaneously determining viability of multiple eggs in an incubation tray are provided herein. A tester unit is locatable entirely above and/or entirely below the incubation tray in close proximity to the incubation tray, or is integrated with the incubation tray. During operation of the tester unit, radiation is emitted into the interior of the eggs. Radiation response associated with a scattered portion of the irradiating/illuminating radiation is sensed as respective signals from the interior of the eggs. The signals are received by a controller which stores measurement data indicative thereof, in real time. The measured data is then processed by the processor.

The incubation tray may be situated in a setting room, or within the eggs incubator, and the testing may be performed in the setting room or the eggs incubator. For instance, in preparation for transfer to a hatching tray, a tester unit according to an embodiment of the present invention, configured as a standalone system, may be located outside the setting room where the testing is performed and a removal mechanism may be subsequently located above the incubation tray. Alternatively or additionally, the tester unit may be placed within the incubator (the tester unit may be integrated in an incubation tray, or may be a standalone system placed above or below a standard incubation tray) to allow testing/inspection of the eggs while within the incubator. In the latter case the controller of the tester unit may be associated with a wireless communication module, such as WIFI or Bluetooth transceiver or other type of wireless communication modules, and may be configured and operable for wirelessly communicating measured data to the processor which may reside in a separate enclosure located outside the incubator.

The eggs may be simultaneously tested to determine the locations within the incubation tray of the viable eggs or of the non-viable eggs. Based on the locations, simultaneous transfer of the viable eggs may be enabled from the incubation tray to a hatching tray while leaving the non-viable eggs in the incubation tray. The tester unit may include a controller and multiple housings/compartments. The housings each include a source of radiation and a corresponding sensor. During the signal processing, a substantial change during a time interval of the signals may indicate that the respective eggs are viable and an unchanging signal may indicate that the respective eggs are non-viable. Based on the stored locations, contact may be avoided with the non-viable eggs during the transfer of the viable eggs.

In some embodiments the controller of the inspection modules is configured and operable to subtract the ambient noise from the signal received from the detector during the measurement time intervals so as to provide the measured signals as noise-corrected signals. This may be achieved by halting emission of the radiation from the emitter prior to the signal processing by the controller, and measuring the ambient noise respectively from the sensors, and then subtracting the ambient noise from the signal obtained from the sensors during the emission of radiation by the emitters.

In some embodiments the controller is adapted to synchronize the operations of different inspection modules so as to avoid cross talk between the inspection modules (e.g. to avoid detection by one inspection module of radiation sourced to the emitter of a different/neighboring inspection module. The synchronization may include operating the inspection (emission and the sensing) of adjacent/neighboring eggs in different time slots to eliminate cross-talk in the signals between the adjacent eggs.

The foregoing and/or other aspects will become apparent from the following detailed description when considered in conjunction with the accompanying figures.

BRIEF DESCRIPTION OF THE DRAWINGS

The invention is herein described, by way of example only, with reference to the accompanying drawings, wherein.

Figure 1A:
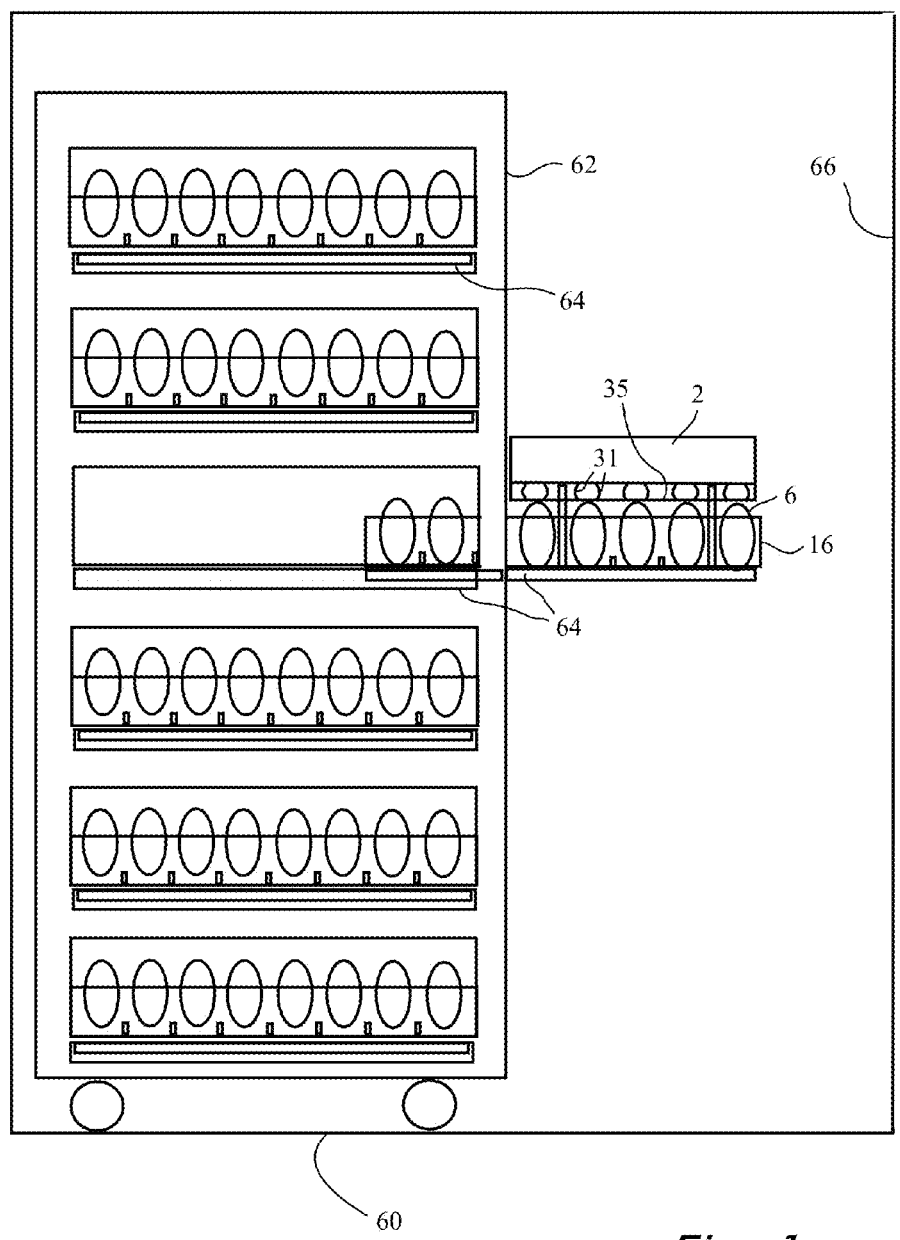
FIG. 1a shows the same tester unit being used to determine viability of a sample of eggs during incubation in the incubator, according to another embodiment of the present invention.

The foregoing and/or other aspects will become apparent from the following detailed description when considered in conjunction with the accompanying drawing figures.

DETAILED DESCRIPTION

Reference will now be made in detail to features of the present invention, examples of which are illustrated in the accompanying drawings, wherein like reference numerals refer to like elements throughout. The features are described below to explain the present invention by referring to the figures.

Before explaining features of the invention in detail, it is to be understood that the invention is not limited in its application to the details of design and the arrangement of the components set forth in the following description or illustrated in the drawings. The invention is capable of other features or of being practiced or carried out in various ways. Also, it is to be understood that the phraseology and terminology employed herein is for the purpose of description and should not be regarded as limiting.

By way of introduction, various embodiments of the present invention are directed to a system and method for determining locations in an incubation tray of viable eggs or the locations of the non-viable eggs, and possibly determining the condition of the viable eggs. The tester unit which determines the viability of the eggs may be based on light/radiation scattering measurements from the interior of the eggs from above or below, so that multiple or all eggs in the incubation tray may be simultaneously tested for viability or monitored by placing the incubation tray with eggs to be tested or monitored under or over the tester unit (or equivalently by placing the test unit over or under the incubation tray with the eggs). Alternatively or additionally the tester unit may be integrated with the incubation tray.

In some embodiments of the present invention, the tester unit is used to monitor development of the embryos of eggs in the incubator. In other embodiments, a tester unit, (optionally the same tester unit) is used a few days prior to hatching in order to remove the viable eggs into a hatching tray for subsequent hatching in a hatchery. The non-viable eggs may be left in the contaminated incubation tray and properly disposed of, and the contaminated incubation tray may be disinfected for reuse.

Advantages of the various embodiments of the present invention over various prior art publications include:

A tray of eggs may be simultaneously processed.

The tester unit, according to embodiments of the present invention, enables candling a large sample of multiple eggs quickly while in the incubator without having to move the eggs in a trolley into a dark room for candling. Moving eggs around is not only time consuming but may contribute to non-viability of eggs due to uncontrolled environments outside the incubator and due to uncontrolled movements of the eggs while being transported in the trolley.

In some implementations (e.g. particularly in cases where the tester unit is configured as a standalone module—not integrated with the incubation tray), contact between the tester unit and the eggs can be avoided during viability testing and therefore viability testing minimizes transfer of contamination from tray to tray. Moreover, it is easier to maintain cleanliness of a non-contact system than that of a contact system.

Testing is performed based on radiation response/scattering from the egg, by illuminating/irradiating the eggs and detecting the radiation response entirely from above or entirely from below the eggs in the incubation tray, or from one or both sides of the egg. Such configurations greatly simplify industrial equipment design.

The tester unit may be configured as a standalone system, and may be placed within the incubator and moved from above/below a first tray for viability testing and on completion the tester unit is moved to a second tray. Prior to hatching, a single conveyor or table may be used to convey the incubation tray from the tester station to the egg removal station.

The tester unit may be integrated in one or more of the incubation trays of the incubator and used to provide complete or statistical data on the condition of the eggs in the incubator.

Referring now to the drawings, reference is now made to FIG. 1a which shows a side view of an incubator 60, according to a feature of the present invention. Incubator 60 has entrance door 66 which provides access to incubation trolley 62. A number of incubation trays 16 are shown in situ. One incubation tray 16 is shown partially slid out on rails 64 to allow placement of viability tester unit 2 above eggs 6. In an alternative embodiment viability tester may have rails in place such that incubation tray 16 when partially slid out on rails 64 allows placement of viability tester unit 2 under eggs 6. In this example a viability tester unit 2 configured as a standalone system (not integrated with the incubation tray) according to an embodiment of the present invention, is also shown together with filter 35. Viability tester unit 2 may further include a wireless transmitter to a wireless local area network (WLAN), e.g. based on a standard of the Institute of Electrical and Electronics Engineers' (IEEE) 802.11, to transmit measured data or data indicative of the viability status of eggs 6 and their locations in incubation tray 16 to a nearby local area network (LAN). Tester unit 2 may include a button (not shown) to initiate a test of multiple eggs and an indicator (LED) (not shown) to initiate and confirm completion of a viability test of eggs 6.

Figure 1B:
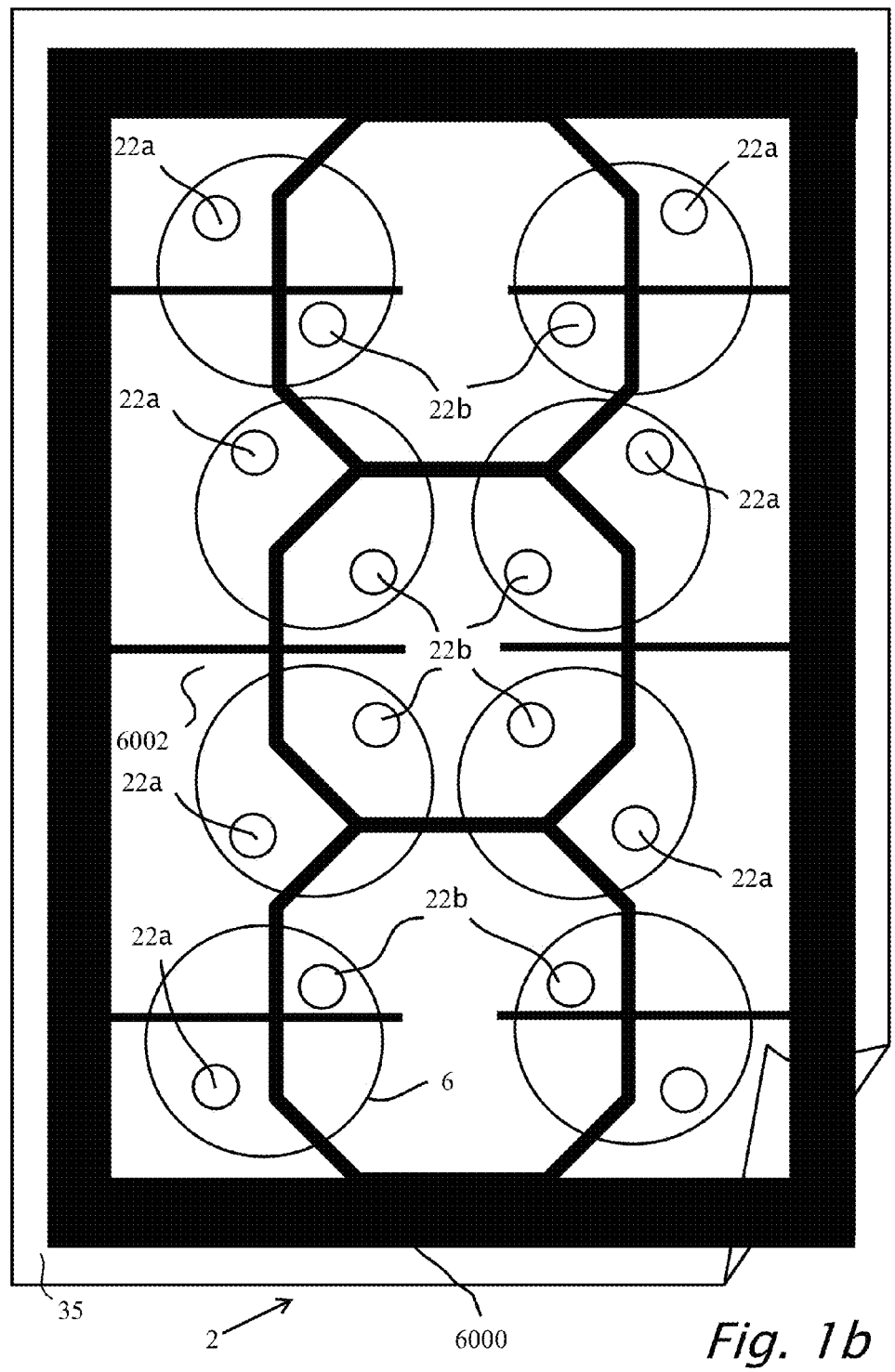
FIG. 1b shows a plan view of a tester unit, according to a feature of the present invention.

Reference is made to FIG. 1b which shows a plan view of tester unit 2, according to a feature of the present invention. In this embodiment the tester unit 2 includes a frame 6000 which provides a surface for the attachment of optical filter film 35 onto frame 6000. Set back from frame 6000 is back plane 6002 which is attached to and/or is an integral part of frame 6000. Back plane 6002 allows for the fixing and mounting of arms 22a and 22b. Positions of eggs 6 are shown with dotted lines relative to respective pairs of arms 22a and 22b. Tester unit 2 is not limited to eight eggs 6 as shown but may constructed to accommodate various numbers of eggs 6 and incubation trays 16 capacities and/or dimensions.

Figure 2:
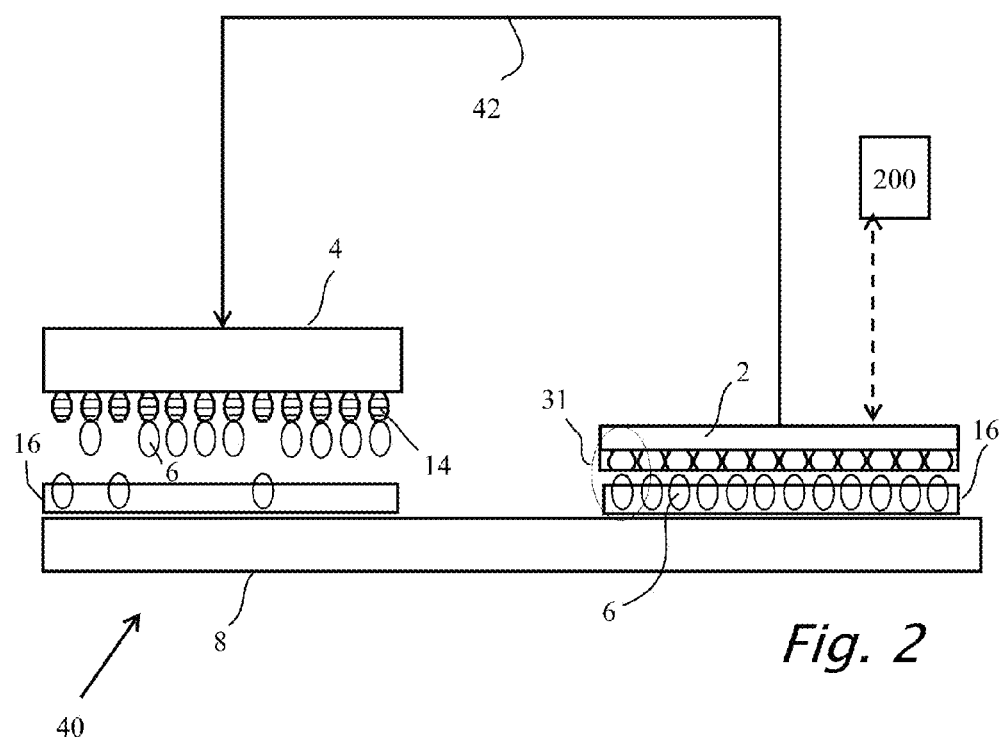
FIG. 2 shows a system block diagram of an eggs processing apparatus for the processing of eggs, according to features of the present invention.

Reference is now made to FIG. 2 which shows a diagram of eggs processing apparatus 40 for the processing of eggs 6, according to another embodiment of the present invention. Eggs processing apparatus 40 is connectable to a processor 200 associated with the egg tester unit 2 according to an embodiment of the present invention and is adapted to receive therefrom data about the conditions/viability of eggs in incubation trays 16. The eggs processing apparatus 40 includes, or is associated with, a conveyor 8 and an egg removal mechanism. The conveyor may be adapted for conveying incubation trays 16 of eggs (e.g. in between an inspection location, at which eggs inspection is performed by the tester unit 2 of the present invention), and the egg removal mechanism. An incubation tray 16 with eggs 6 is shown placed under viability tester unit 2 which includes multiple inspection modules 31. Eggs processing apparatus 40 obtains from the processor of the tester unit 2 data on the conditions/viability of eggs and their locations in the incubation tray, and operates the conveyor and the egg removal mechanism to remove eggs from these locations. Another incubation tray 16 is shown where a removal mechanism 4 has removed some viable eggs 6 from incubation tray 16 by use of actuators 14. Some of the suction cups 14 of the egg removal mechanism may be activated so as to pick up viable eggs 6 and other suction cups 14 are not activated leaving non-viable eggs 6 in incubation tray 16. A data connection 42, optionally a wireless connection, may connect viability tester unit 2 to the processor, and/or to the removal mechanism 4. The locations/tags of the viable and/or non-viable eggs 6 in incubation tray 16 may be passed via data connection 42 to removal mechanism 4 so that only viable eggs 6 are transferred to a hatching tray.

Alternatively or additionally, the locations/tags of the in incubation tray 16 may be flagged/indicated for instance by using a flagging system adapted to provide/display indication/listing on the location of the viable and/or non-viable eggs 6. A flagging system of this type may be integrated with the incubation tray and may include a plurality of indicators (e.g. indicator LEDs and/or other indicator/flag modules located adjacent to the location of the eggs in the tray). A flagging system may include a flagging control system capable of communication with the processor to receive therefrom the location of the viable/non-viable eggs in the tray. With response to receipt of these locations, the flagging control system may operate the indicators (LEDs) of the viable and/or of the non-viable eggs to indicate the condition of each egg (which of the eggs is viable/not-viable). A flagging system of this type is illustrated for instance below with reference to FIGS. 12a and 12b, in which an incubation tray 16 integrated with a tester unit according to an embodiment of the present invention is shown. It should be however understood that in similar manner such a flagging system may be integrated with an incubation tray that does not include the tester unit 2. In such cases a tester unit of the invention configured as a standalone module (such as that shown in FIGS. 1a and 1b) may be used to test the condition of the eggs in the tray and to provide measured data indicative of the same to the processor which, in turn, determines the condition of the eggs in the tray and communicates the same to the flagging system (which may be integrated in the tray).

Figure 3:
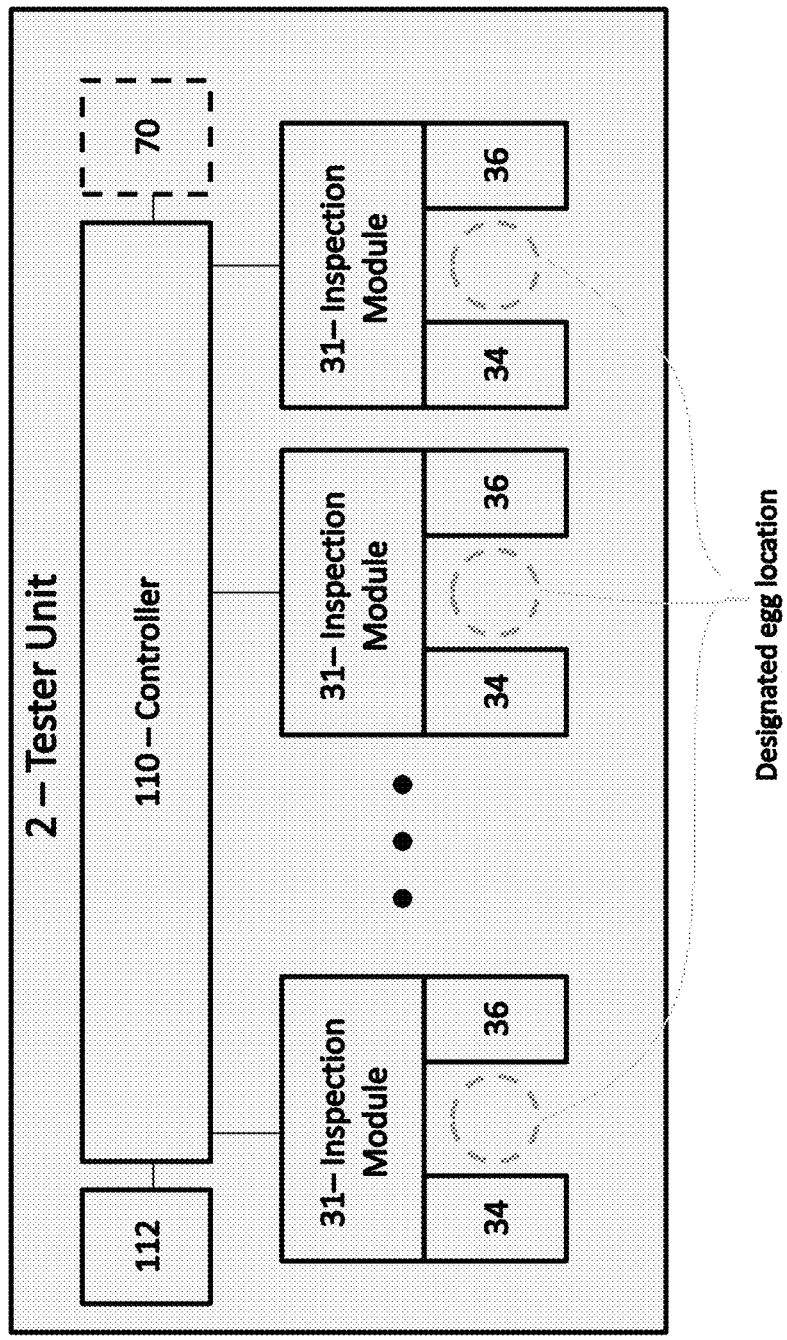
FIG. 3 is a block diagram exemplifying the configuration of a tester unit according to an embodiment of the present invention.

Reference is now made to FIG. 3 showing a block diagram of a tester unit 2 according to an embodiment of the present invention. The tester unit 2 includes a controller 110 (or plurality of controllers) associated respectively with a plurality of inspection modules 31 each adapted for inspecting an egg. The plurality of inspection modules 31 may be arranged in an array with pitches corresponding to the pitches between eggs (egg placements) in an egg tray in which egg inspection is to be conducted. Each inspection module 31 includes an emitter 34 (or plurality of emitters) adapted for emitting radiation (electromagnetic or acoustic) towards a designated location of an egg to be inspected by the respective inspection module 31, a sensor 36 (or plurality of sensors) adapted for sensing radiation (electromagnetic or acoustic) arriving from a designated location of an egg in response to the emission of the radiation by the emitter 34. The controller 110 is connected to the inspection module 31 and is adapted to operate the emitter 34 to emit radiation towards the egg and obtain the signal sensed by the sensor 36 indicative of the radiation response from the egg. The detected signals give rise to measured data indicative of the condition of the egg inspected by the respective inspection module 31.

As will be further described below in more detail, the tester unit of the invention may be configured as a standalone module, which is to be located above or below a tray of eggs to inspect the eggs therein (e.g. in reflection mode from one side above or below the eggs, along their longitudinal axis), or it may be integrated in the egg tray and adapted for inspecting the eggs from one or both sides (in reflection/transmission modes).

In some implementations, the emitter 34 is configured to emit electromagnetic (EM) radiation in the optical regime, such as IR (e.g. Near IR) radiation. The emitter may be for example a radiation source, such as a laser or a light emitting diode (LED) operative to emit EM radiation in this regime, and/or a wave guide (such as an optical fiber) connected to such a radiation source. The sensor 36 is configured and operable to sense/detect radiation in this optical/IR regime and may include photosensitive elements such as a photodetector/photodiode. The emitter 34 and sensor 34 are arranged with respect to the designated location of the egg which is to be inspected such that the signals detected/measured by the sensor, are indicative of radiation scattered from the interior of the egg (e.g. from the embryo). Accordingly, as further discussed below, the detected signals may be processed to determine the size/growth of the embryo and/or its physiological development stage.

In some embodiments of the present invention the tester unit 2 is also configured and operable for monitoring certain aspects of the incubation conditions and/or the operation of the incubator. For instance, conventional incubation techniques include turning (e.g. rolling and/or tilting) the eggs during the incubation period, in order to optimize the incubation results. The egg-tilting and/or egg-rolling operation of the incubator has significant impact on the incubation outcome. Therefore, in some implementations of the present invention the tester unit 2 optionally includes a tilt/roll sensor(s) 70, which is adapted to measure the degree of tilt and/or the roll rate of the eggs during the incubation. The tilt/roll sensor(s) 70 may be for example implemented by an accelerometer that is capable of measuring the angle of tilt of the eggs (of the eggs incubation tray), and/or alternatively or additionally, by a gyroscope sensor, capable of measuring the roll (rotation/turning) rate of the eggs. The tilt/roll sensor(s) 70 may be for example implemented in (e.g. located on/within and possibly integrated with) the incubation tray of the eggs, and/or in the enclosure of the tester unit 2 in case the later is implemented as a standalone module which is to be located on/above the incubation tray (parallel to the surface thereof). The tilt/roll sensor(s) 70, may be connected to the controller 110 who, in turn, receives therefrom measured tilt data indicative of the eggs tilting, and/or turning/rolling rate(s), during periods of the incubation and stores that data (e.g. in locale and/or remote memory/storage) for further processing by which the quality of the incubation conditions can be determined, possibly enabling to utilize the measured tilt data for adjusting the operation of the incubator for turning the eggs (e.g. in real time during the incubation process).

In some embodiments of the present invention the tester unit 2 is also configured and operable for communicating the measured data and/or the measured tilt data to an external processing system (processor). To this end, the tester unit 2 may include a communication module 112, which may be a wireless communication module configured and operable for establishing communication between the controller 110 and the external processing system such that the measured data and/or the measured tilt data can be processed by the external processing system to determine the conditions of the eggs (e.g. the conditions of the embryos therewithin) and/or the incubation conditions (e.g. the egg tilting/rolling conditions). Use of wireless communication module allows the external processing system (processor) to process data obtained from the tester unit 2, while the later is placed within the incubator (e.g. as a standalone unit or integrated within the incubation tray of eggs.

In some implementations, the emitter 34 is configured and operable to emit radiation in the RF regime. In this case the emitter may be, for example, an antenna connected to an RF transmitter. The sensor 36 may be also be an antenna (e.g. the same antenna of the emitter or a different one) associated with a receiver of RF signals. To this end in some embodiments the tester unit 2, and the inspection modules 31 thereof, are configured and operable to carry out Nuclear Magnetic Resonance (NMR) and/or Magnetic Resonance Imaging (MRI) measurements. The eggs under test may be subjected to the influence of a strong magnetic field, for example by using a magnetic field source (not specifically shown) associated with the tester unit (e.g. located for example in the incubator/tray in which eggs are being tested). The emitter 34 may be adapted to emit pulses of RF radiation towards the egg, and the sensor 36 adapted to detect radiation response from the egg in the form/frequencies of electromagnetic field/radiation that is associated with the magnetic resonance caused by the combination of the strong magnetic field and transmitted RF radiation. Measured data on the magnetic resonance of the material of the eggs is then further processed according to conventional MRI or NMR techniques and used to determine data indicative of the condition of the egg/embryo thereinside.

In some implementations, the emitter 34 is configured and operable to emit acoustic radiation/waves towards the egg, the sensor 36 sensing scattered acoustic radiation coming from the egg in response. In this case the emitter 34 and sensor 36 are configured and operable as acoustic transducers. In some implementations the emitter 34 and sensor 36 operate in interleaved time intervals to transmit and receive radiation to the egg. In this case, optionally, the same transducer may by used as both emitter 34 and sensor 36. In some implementations, the emitter 34 and/or the sensor 36 include directional acoustic transducers (such as phased array transducers) capable of respective directional emission of detection of acoustic radiation (e.g. focused) to one or more regions in the egg. In this case the inspection module 31 may be adapted to perform acoustic scanning of the egg (e.g. of its outer shell surface and/or of its content) to obtain measured data indicative of the integrity of the egg shell and/or of the condition of the embryo inside the egg.

Reference is now also made together to FIGS. 4a to 4d which show a sub-system 31 (also referred to herein as egg inspection module) of tester unit 2, according to certain embodiments of the present invention. Egg 6 is irradiated/illuminated with radiation from source/emitter 34. In these examples the egg inspection module 31 also includes one or more sensors/detectors 36 configured as EM sensors. The emitter 34 may be located in an arm 22b. The sensor(s) 36 may be located in an arm 22a. The emitter/source 34 and the sensors/detectors 36 (e.g. arms 22a and 22b) may be located/connected to a single housing of the tester unit 2 which corresponds to a single egg 6 in incubation tray 16.

In some embodiments, the emitter(s) 34 outputs EM radiation and the sensor(s) is an EM sensor. Accordingly, and without loss of generality, in the examples below emission and detection of EM radiation, such as optical IR radiation, is particularly considered. However it should be understood that the principles of the present invention as described below may also be implemented with other radiation types, such as acoustic waves and/or EM radiation in the RF regime.

The electromagnetic radiation source/emitter 34 may be a light emitting diode (LED), and/or a laser and/or and antenna and/or possibly a wave guide such as an optical fiber. For clarity, and without loss of generality, the source/emitter 34 is also referred to hereinafter as LED 34. LED 34 may be a High Power Infrared LED, part No. SFH 4550, OSRAM Opto Semiconductors GmbH Wernerwerkstrasse 2, D-93049 Regensburg, Germany. Radiation sensor 36 may be a photodetector, such as a photo diode (PD), and/or an antenna. For clarity, and without loss of generality, the radiation sensor 36 is also referred to hereinafter as PD 36. Photo diode PD 36 may be a Silicon PIN diode, S6036 series, HAMAMATSU PHOTONICS K.K., Solid State Division, 1126-1 Ichino-cho, Higashi-ku, Hamamatsu City, 435-8558 Japan. LED 34 may emit radiation, such as light at near infra-red (NIR) optical wavelengths (e.g. between 600 and 950 nanometers). The PD 36 may be a silicon photo-diode sensitive at corresponding NIR optical wavelengths (between 600 and 950 nanometers).

Figure 4A:
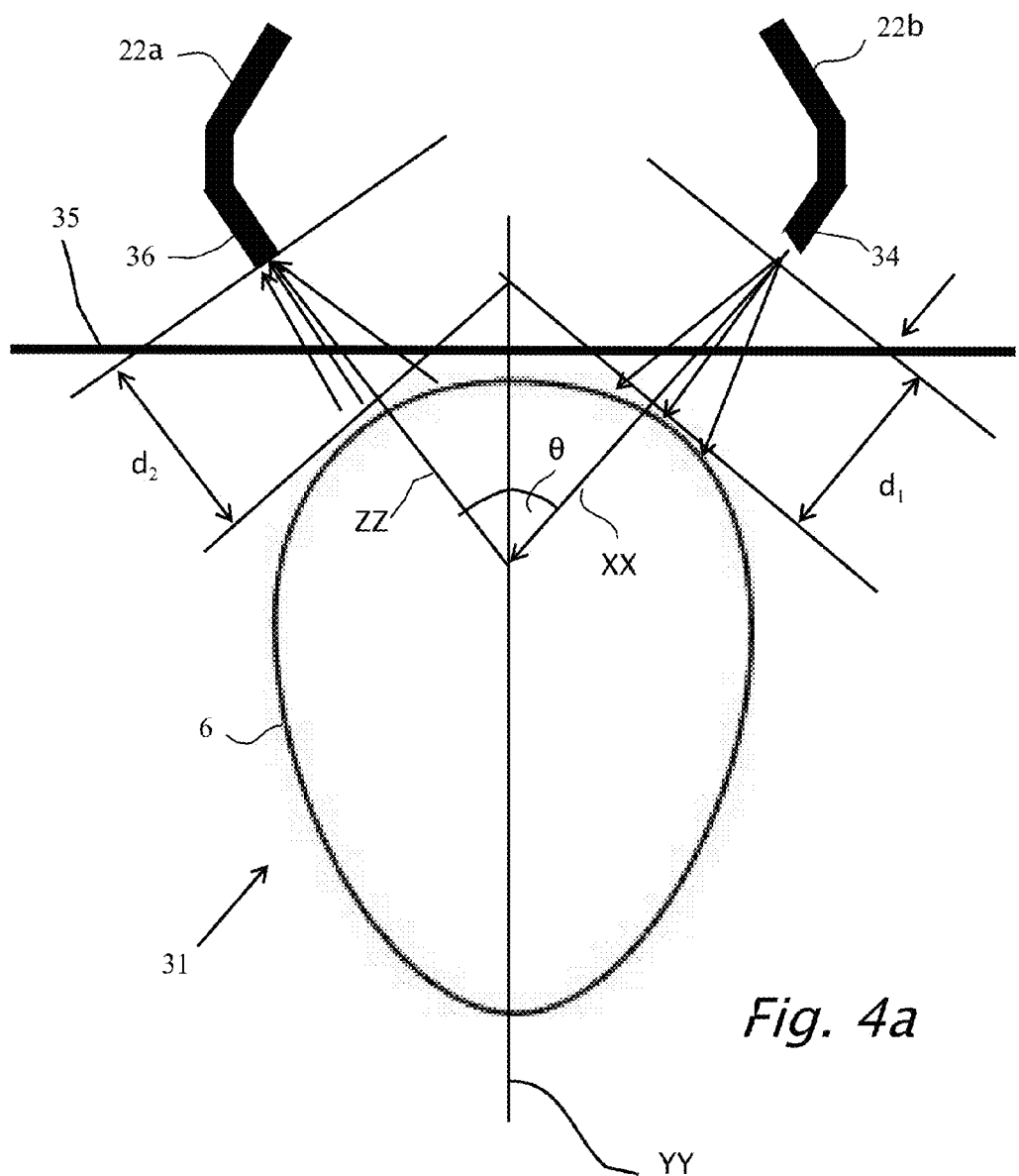
FIGS. 4a to 4d show four possible configurations of inspection modules according to embodiments of the present invention, for testing eggs' condition/viability.
Figure 4B:
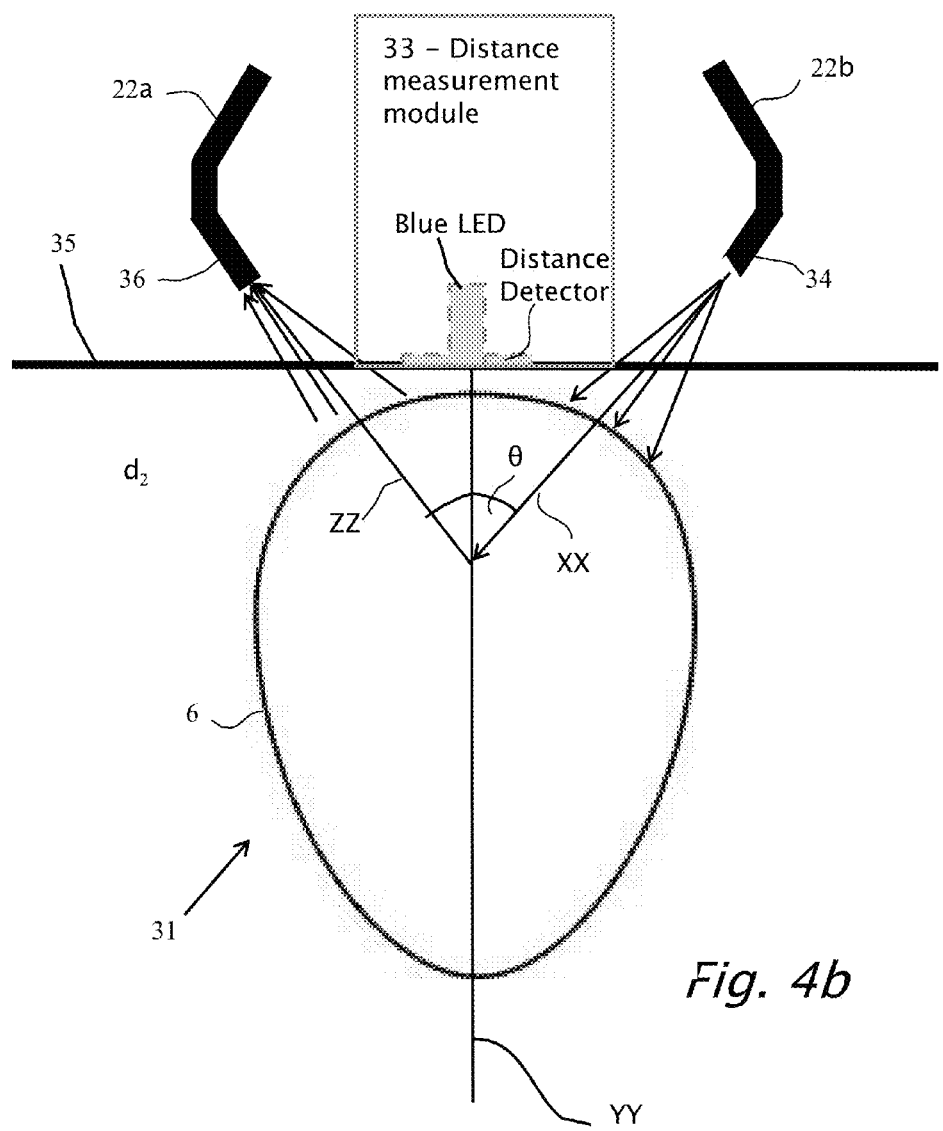
Figure 4C:
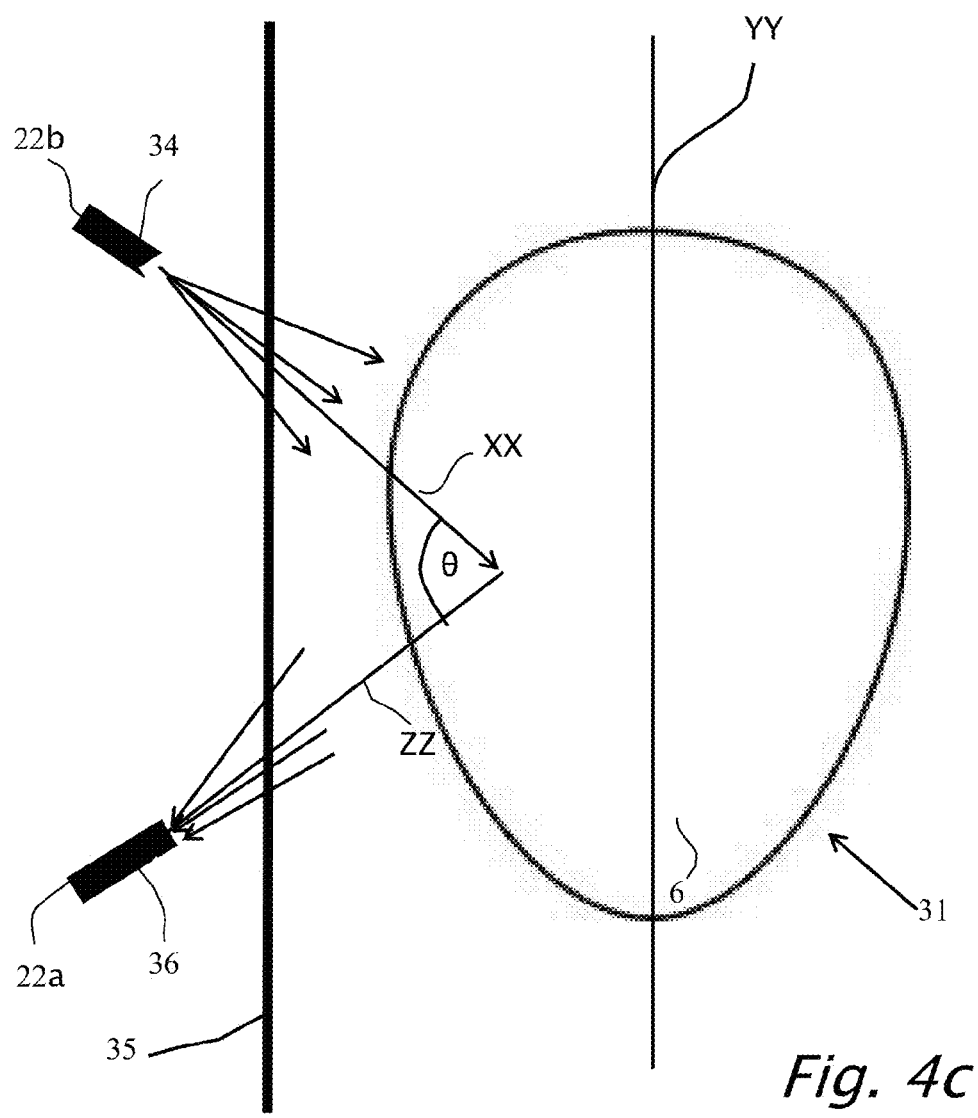

In this example of FIGS. 4a to 4c, the inspection module is configured and operable for inspecting an egg from one side of the egg (e.g. from the top or bottom or lateral side thereof). More specifically the inspection module is configured such that illumination and detection of the radiation response from the egg are performed from the same side of the egg. The inspection module 31 is configured such that the illumination path/axis XX, being the center of the emitted beam of LED 34, and the detection path/axis ZZ, being the center of the field of view of reception of PD 36 are tilted with respect to one another by an angle θ in order to prevent/reduce detection of reflections (speculare reflections) from the egg shell. To this end, the LED 34 and the PD 36 (e.g. arms 22a and 22b) may be positioned such that angle θ between axes XX and ZZ may vary between 50 and 120 degrees between axes XX and ZZ. Alternatively, angle θ may vary between 60 and 110 degrees, or between 70 and 100 degrees. Illumination rays of egg 6 by LED 34 are shown by arrows with solid lines and scattered radiation/light sensed by PD 36 is shown by rays with dotted lines. Although a single ray of singly scattered radiation/light is shown, the scattered radiation/light entering and being sensed by PD 36 may be singly or multiply scattered within egg 6. The signals of the scattered radiation measured by the PD are obtained by a controller (not shown) of the inspection module 31 and used as the measurement data, which is then further processed to determine the condition of the egg.

The inspection module 31 shown in FIGS. 4a and 4b, is specifically configured for use in a standalone tester unit, such as the tester unit shown in FIGS. 1a and 1b, which is adapted to be placed above or below an incubation tray for testing the eggs therein, where the eggs are placed in the incubation tray such that their longitudinal axis (their long axis) is substantially vertical. The longitudinal axis YY of egg 6 is shown in FIGS. 4a and 4b. The inspection module 31 is configured such that during normal operation, arm 22b housing LED 34 and arm 22a housing PD 36 avoid contact with egg 6 and are separated from the shell of egg 6 by distances $d_1$ and $d_2$ respectively. In some embodiments the inspection module 31 is configured such that the LED 34 and PD 36 can be spaced from the egg by a planar wall/filter 35. The radiation intensity from LEDs 34 for testing of eggs 6 in the earlier stage of incubation may be less than the radiation intensity from LEDs 34 used during later stages of incubation; during the earlier stage eggs 6 are more clear. In any case, the radiation level may be adjusted to avoid saturation in photodiodes 36. Optical filter film 35 may be optionally placed between egg 6 and arms 22a and 22b. Optical filter film 35 may be absorptive, dichroic, monochromatic, infrared, ultraviolet, polarizing, guided, long-pass, short-pass, neutral density, bandpass or any optical filter known in the art.

It should be understood that in some embodiments, more than one sensor can be used to detect the radiation response from the egg. This allows detection of radiation response from several locations of the egg, thus reducing the effects of the embryo posture within the egg, on the measurements results. The measured radiation response from the one or more sensors of the inspection module may be summed by the controller (not shown) of the inspection module and serves for generating the measurement data indicative of the condition of the egg. It should be also noted that in some embodiments more than one radiation/light emitter (LED) may be included in the inspection module.

FIG. 4b shows an egg inspection module 31 according to another embodiment of the present invention. Here an inspection module 31 with similar configuration as that described above with reference to FIG. 4a is shown, including, additionally, a distance measurement module 33 which is configured and operable to measure the distance to the egg under inspection. The distance measurement module 33 may for example include an emitter of light (e.g. LED of blue light which is mostly reflected from the egg shell) and a corresponding detector for detecting the reflection. A distance to the egg may be determined for example by measuring the time of flight of the light to and from the egg shell. According to this embodiment the measured distance to the egg shell is used in the processing of the intensity of the radiation response to determine the condition of the egg with improved accuracy (considering the radiation response is proportional to the inverse of the squared distance, and thus the further the egg, the lower would be the intensity of the radiation response for a given illumination intensity and given condition of the egg).

The configuration of the inspection modules of FIGS. 4a and 4b in which inspection is performed from above or below the egg are particularly suited for use in tester units that are configured as standalone devices, such as that shown in FIGS. 1a and 1b, which are placed, during operation, above or below the incubation tray of the eggs.

Figure 4D:
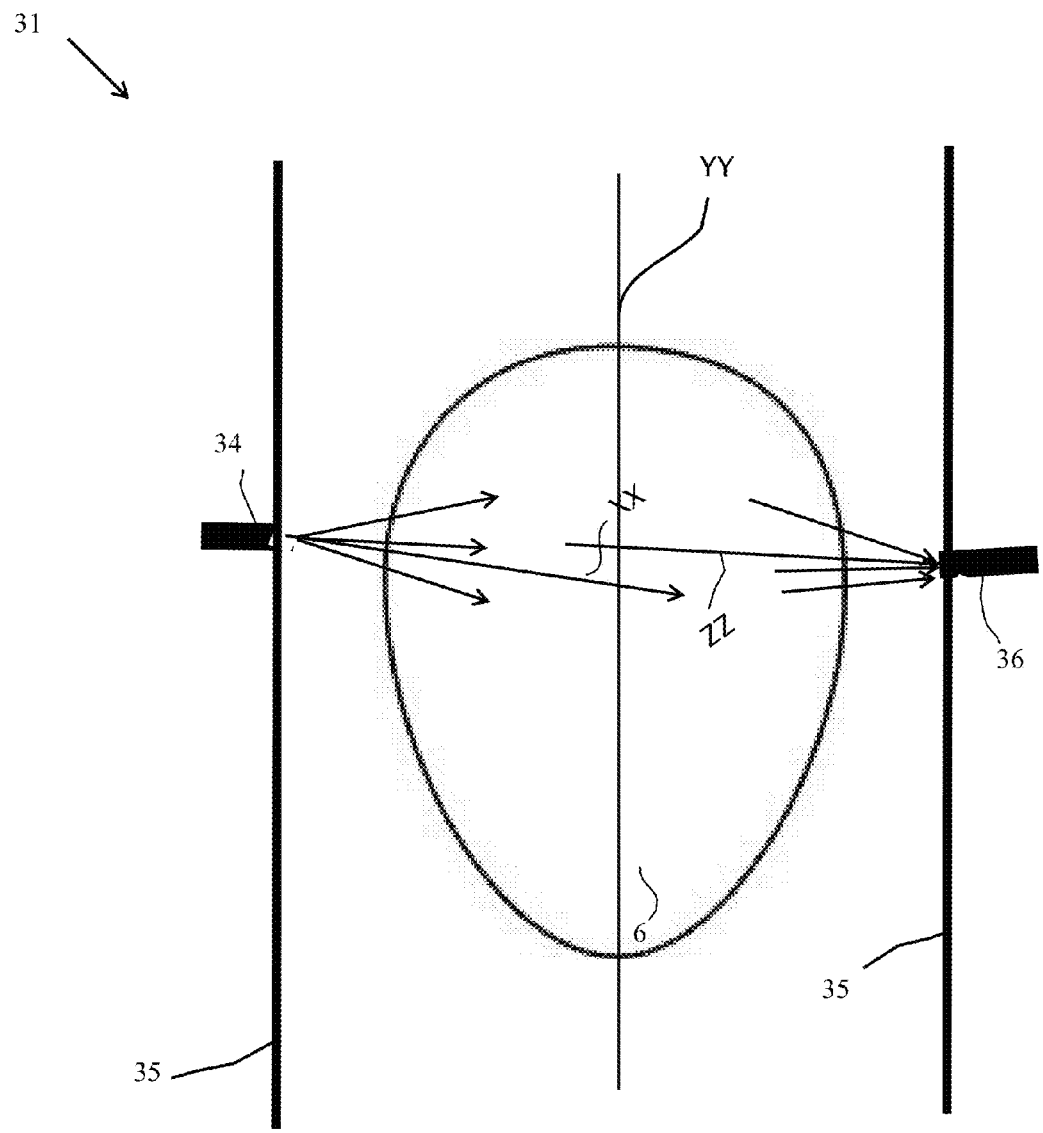

FIGS. 4c and 4d show two examples of egg inspection modules 31, according to two embodiments of the present invention. In these examples the inspection modules 31 are configured and arranged for inspecting the egg from its lateral side (e.g. across a transverse/horizontal plane of the egg intersecting the longitudinal/axis YY of the egg). Such configurations, where the eggs are inspected from their side, are particularly suited for use in tester units that are integrated with the incubation trays. This is because it allows to place the inspection modules 31 on the side(s) of the eggs, while enclosing them in side walls of the incubation tray that are located between the egg locations, in a manner that facilities proper ventilation of the incubated eggs while preserving the regular/standard dimensions of the incubation tray (specifically thickness) such that it fits the standard incubators, and also maintaining the same capacity of eggs as in the standard tray of the same size. This is described in detail below with reference to FIGS. 5a and 5b.

It is noted that in the embodiment of FIG. 4c the inspection module is configured to inspect the egg from one side thereof, by illuminating the egg from that side and detecting the electromagnetic radiation scattered back from towards the same side. Accordingly, in this embodiment the emitter 34 and sensor 36 may be configured and arranged such that their illumination and detection paths are tilted with respect to one another by an angle θ (e.g. being between 50 to 120 degrees).

It should be noted that embodiments of the invention in which the inspection modules are configured to illuminate and detect the radiation response from the egg from the same side (hereinafter referred to as reflection mode of operation), such as those illustrated in FIGS. 4a to 4c, may be advantageous for use in portable/standalone implementations of the testing unit, since it allows performing the measurements from one side of the eggs (e.g. the top and bottom), and therefore facilitates compact and easy to use packaging of the tester unit in a single compact enclosure.

In this regard it should be noted that the inventors have found that operating in the "reflection mode" is suitable for measuring dynamic parameters of the radiation scattering from within the egg. More specifically, in the reflection mode, as well as in the transmission mode, the signal/voltage obtained from the sensor 36 can be processed to accurately measure/determine frequency content in the AC components of the signal. A processor connectable to the testing unit may be configured and operable to process/analyze the AC component of the signal to identify existence of periodic variations in the scattering (radiation response) form the egg, and the prominent frequencies of periodic variation. As described in detail in PCT patent publication no. WO2015145435, the condition of the incubated egg and/or its embryo can be determined based on the frequencies identified in the AC component of the signal (the frequencies of the periodic variations) to assess the condition of the embryo (viable/non-viable) and/or its development stage. This is discussed in more detail below with reference to FIGS. 5a and 5b.

In the embodiment of the egg inspection module 31 shown in FIG. 4d, the emitter and detector are located from opposite sides of the designated location of the egg that is to be inspected thereby. The inspection modules are configured and operable to illuminate the egg from one side thereof, and to detect the radiation response from the interior of the egg, from the opposite side. This is referred to hereinafter as the transmission mode of operation. It should be noted that the transmission mode of operation facilitated by the configuration shown in FIG. 4d advantageously facilitates accurate measurements of the amount (intensity) of radiation scattered from the interior egg (e.g. analyzing the transmittance through the egg), while being less susceptible to the effects of reflections from the egg shell (since in this mode the transmittance through the egg is measured). Accordingly, since in this mode reflection from the egg shell substantially does not impair the measurement, therefore the illumination and detection paths in this configuration need not be necessarily tilted at any particular angle with respect to one another.

It should be noted that the configuration of the inspection modules shown in FIG. 4d facilitates measuring the dynamic parameters described below with reference to FIG. 5b. Also, since inspection modules configured according to FIG. 4d operate in transmission mode (in which case the effects of reflections from the egg shell are reduced), therefore this configuration also enables accurate measurements of the egg's transmissivity/opacity (transmittance through the egg), by measuring the amount/intensity of the radiation response passing through from the interior of the egg. The egg's transmissivity can be measured accurately by processing signal/voltage obtained from the sensor 36 to determine the magnitude of the DC component of the signal. For a given intensity of the radiation from the emitter, the DC component of the signal is proportional to the transmissivity of the egg, and therefore becomes smaller as the embryo grows. This is discussed in further detail below with reference to FIGS. 5a and 5c.

Figure 5A:
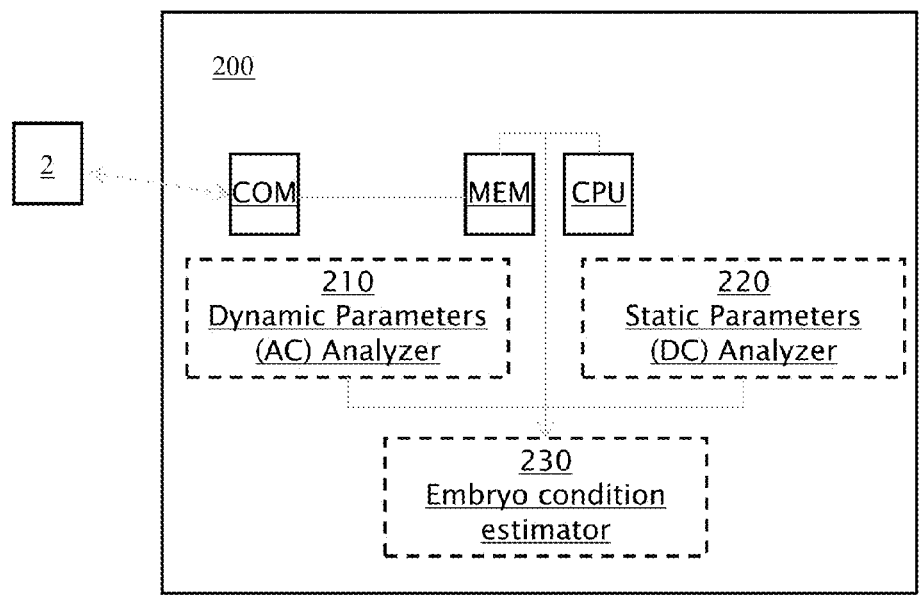
FIG. 5a is a block diagram of a processing system configured and operable according to the present invention for processing measured data about the radiation response from eggs to determine the condition of eggs, based on at least one of dynamic and static parameters of the radiation response from the eggs.
Figure 5B:
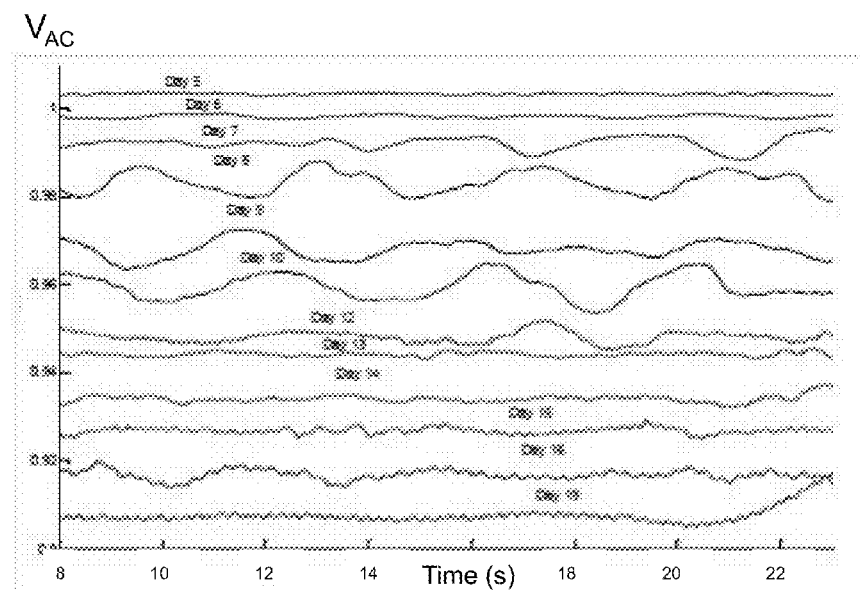
FIG. 5b exemplifies graphically a relation between dynamic parameters of the radiation response of an egg and a physiological development stage of an embryo within the egg.

Reference is made to FIG. 5a which is a block diagram of a processing system 200 (processor) according to an embodiment of the present invention, which is configured and operable for processing the measured data obtained from a tester unit 2 of the present invention. As indicated above, the tester unit 2 may include a plurality of inspection modules (not shown) arranged for measuring the radiation response from a plurality of eggs, and a controller, adapted to obtain the signals from the sensors of the inspection modules and to generate measured data on the plurality of eggs. The controller may be associated with a wired or wireless communication module adapted to provide measured data to the processor 200 at which the measured data of each egg can be processed to determine the condition of the egg.

Typically, the processor 200 is implemented as a computerized system (e.g. including a central processing unit CPU and a memory MEM). The processor 200 may include a wireless and/or wired communication module COM adapted for receiving the measured data from the tester unit 2. The measured data of the eggs is stored in the memory in association with the egg to which it is related (the egg may be indicated by the identification/number of the measured incubation tray and the location in the tray and possibly also the date on which inspection of the egg is conducted). For a given egg, a plurality of inspections may be performed on different days during the incubation period. The measured data from the plurality of inspections may thus be stored in the memory of the processor 200 at different times.

Optionally, the processor 200 includes a dynamic parameter analyzer 210 that is adapted to process the measured data of the eggs to identify the dynamics (the AC components) of the radiation responses from the eggs obtained during given one or more inspection(s) of the egg. The measured data of each inspection may be processed independently to determine the dynamic parameters of the radiation response from the egg during inspection. To this end, dynamic parameter analyzer 210 is configured and operable to analyze the measured data obtained at the given inspection and identify the periodicities/frequencies of variations in the intensity of the radiation response from the egg during the inspection. This may be achieved for example by applying Fourier Transform to the measured data obtained from the sensor during the inspection, and identify prominent peaks in the Fourier transform, which correspond to the prominent frequency (AC) components.

The dynamic parameter analyzer 210 may be associated with reference data (e.g. stored in the memory MEM) indicative of the dynamic response from the egg at different stages of development. For instance, FIG. 5b shows graphs each presenting typical radiation responses obtained during 15 second inspections of the egg which are carried out on different incubation days. A first empirically measured development stage identified in the inspections, which corresponds to the radiation response from the egg from the time it is placed in the incubator to approximately the seventh day of incubation. Until that time (see for instance the graphs of Days 5 and 6) none or only minor AC components appear in the inspection signal. On about the $7^{th}$ day periodic AC component(s) (e.g. with frequency between 0.1 and 0.4 Hertz) become apparent in the measured signal. These components, which may be possibly attributed to the breathing cycle, are indicative of a live or viable embryo/chick in the eggs. The absence of periodic signals around day seven is an indication of possible unfertilized eggs or eggs which have been fertilized but are not alive. A second empirically measured development stage of the embryo is expected to be identified on about the thirteenth day, on which periodicity in measured radiation response starts to vanish, while yet the monitored signals seem to change randomly in time (which is also indicative of a viable egg). A third development stage of the embryo is expected on about the $17^{th}$ day of the incubation, and is characterized by appearance of the noticeable periodicity of higher frequency component (between 2 and 5 Hertz) which corresponds to heartbeat frequency.

Thus, according to some embodiments of the present invention the dynamic parameter analyzer 210 is adapted to utilize the identifying the periodicities/frequencies in the intensity of the radiation response from the egg, to determine the development stage of the egg and whether a live embryo exists therewithin. It is noted that in order to obtain reliable reading of the dynamic parameters/frequencies of the radiation response, the egg should be preferably inspected for duration of at least a few seconds (e.g. 5 seconds or more and more preferably 15 seconds or more) at each inspection session. Inspection sessions may be conducted on a daily basis or every few days to monitor the development stage of the embryo during incubation. The dynamic parameter analyzer 210 utilizes the dynamic parameters of the radiation response to determine development stages corresponding to physiological changes in the embryo.

Figure 5C:
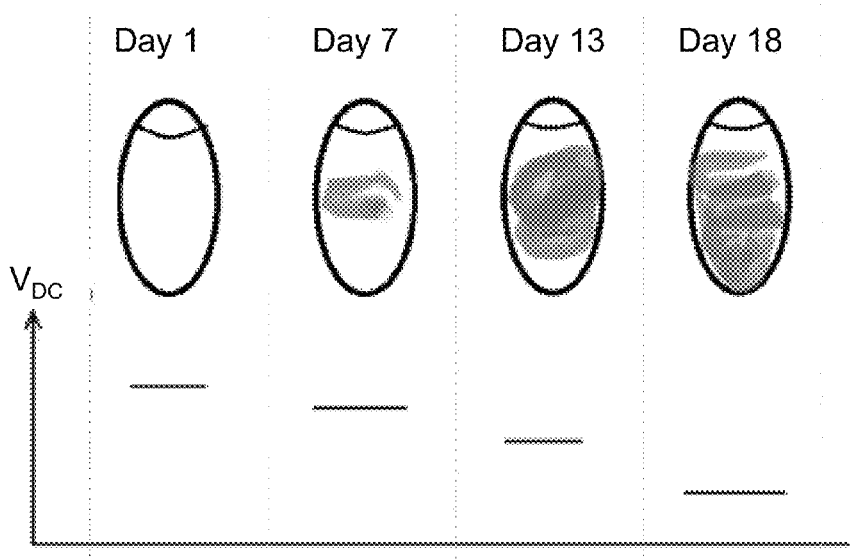
FIG. 5c exemplifies graphically a relation between static parameters of the radiation response of an egg and growth/size of an embryo within the egg.

Optionally, the processor 200 includes a static parameter analyzer 220 that is adapted to process the measured data of the eggs to identify the static (the DC components) of the radiation responses from the eggs obtained during given one or more inspection(s) of the egg. The measured data of each inspection may be processed independently to determine the magnitude of data indicative of the DC component (e.g. time average intensity) of the radiation response obtained at each inspection, or, in some cases, determine a normalized DC component for example by determining a ratio between the DC component (or time average intensity) of the radiation response and the intensity of the illumination from the emitter 34) parameter of the radiation response from the egg during inspection. The DC component of the radiation response is generally indicative of (e.g. with inverse proportion to) the size of the embryo within the egg, since it is a measure of the transmissivity/opacity of the egg. Accordingly by processing the measured data obtained from an inspection of the egg on a certain incubation day, and determining the intensity of the response (the DC component), the size of the embryo within the egg can be estimated. FIG. 5c exemplifies, in a self explanatory manner, the relation between the magnitude of the DC components (in this case provided in terms of the voltage of the signal provided from the sensor 36) and the expected size/incubation day of the embryo. To this end, the static parameters of the radiation response may be used to provide indication of the growth in size of the embryo.

In this regard, in some embodiments the static parameter analyzer 220 may utilize reference data relating the expected opacity of the egg as a function of the incubation day, to estimate whether the embryo within the examined egg is properly developed according to the corresponding incubation day.

Alternatively or additionally, in some embodiments the static parameter analyzer 220 is configured and operable to store, in a memory, history data about the magnitudes of the DC component (or normalized DC components) measured on different incubation days (corresponding to different inspection sessions of the egg), and utilize this history data to assess whether the embryo is growing properly within the egg, or its growth is halted or disturbed, which may indicate a bad or dead embryo.

The static parameter analysis (to determine the growth/size of the embryo based on the DC component) is preferably and more accurately carried out when inspection of the eggs is performed in transmission mode indicated above (e.g. by using the inspection module of the embodiment of FIG. 4d described above). This is because in this case the measured DC component of the radiation response is more accurate and less affected by noise associated with radiation reflections from the shell. Further, when operating in transmittance mode, it is preferable and more efficient to measure the transmittance of the egg from its lateral side (and not from along its longer longitudinal axis), at least because it requires lower illumination intensities.

It should be understood that in some embodiments of the present invention the processor 200 may include only the dynamic parameter analyzer 210, and data on the condition of the eggs in the tray is determined by analyzing the dynamic parameters (AC components) of the radiation responses from the eggs indicative of the physiological development stage of the embryo. Alternatively in some embodiments of the present invention the processor 200 may include only the static parameter analyzer 220, and data on the condition of the eggs in the tray is determined by analyzing the static parameters of the radiation responses from the eggs indicative of the growth/size of the embryo. Yet, in some embodiments the processor 200 includes both dynamic and the static parameter analyzers, 210 and 220, and possibly also an embryo condition estimator 230 that is configured to receive the processing results of the analyzers 210 and 220, and to determine the condition of the egg/embryo, by determining whether there is agreement between the results of the analyzers 210 and 220 (determining whether the growth/size of the embryo corresponds to its physiological development stage), and/or whether their results correspond to the incubation day of the embryo (on which the inspection session is performed). Accordingly, the processor may output data indicative of the conditions of the eggs according to their location in the incubation tray and/or data indicative of the viability of the embryos within the eggs.

Figure 6:
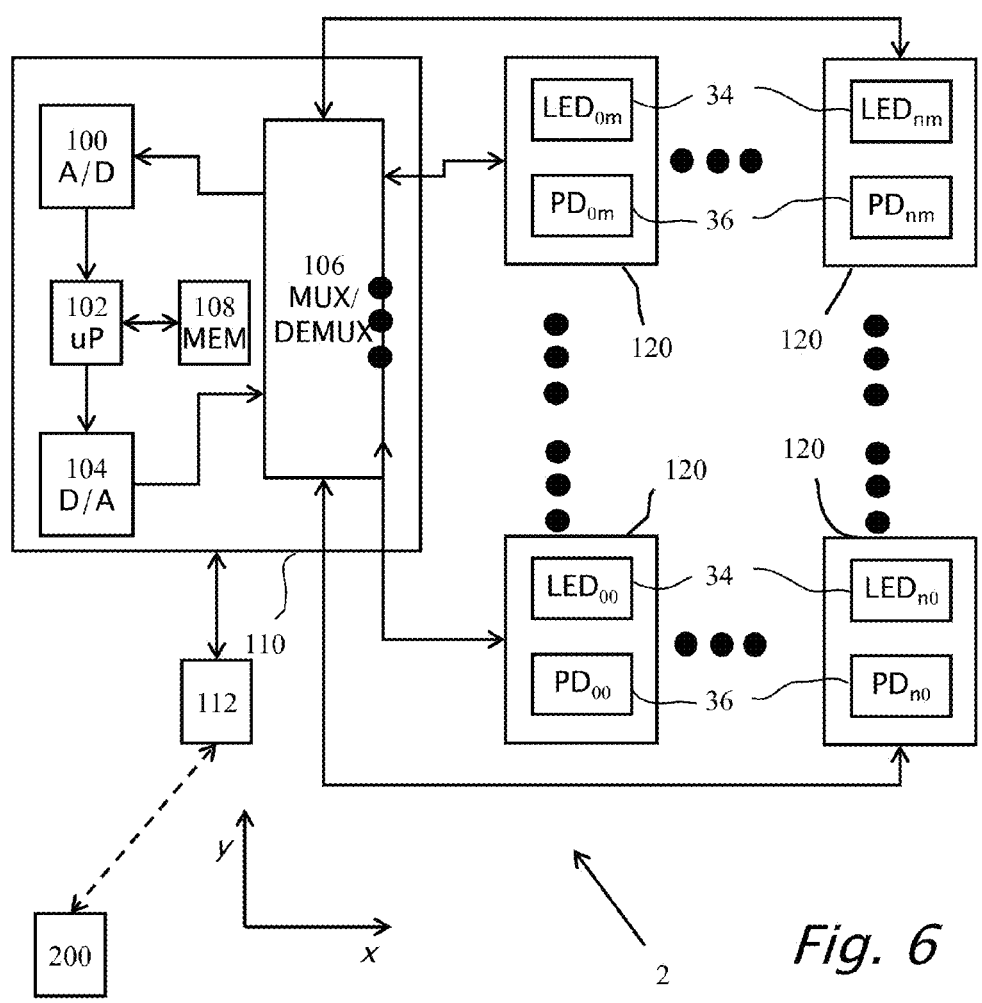
FIG. 6 shows a system block diagram of a system including a tester unit used to determine the viable status of eggs, according to a feature of the present invention.

Reference is now made to FIG. 6 which shows a simplified system block diagram for a tester unit 2 used to determine individually the viability of multiple eggs 6, according to a feature of the present invention. Tester unit 2 includes a plurality of inspection modules 31, 36 for testing multiple eggs, each including at least one LED 34 and at least one PD. In this example the inspection modules 31 are enclosed/located in respective housings 120, each defining an egg placement (e.g. dimples, not shown in the figure) at which an egg can be accommodated for inspection. The housings 120 (and the egg placements) are shown as arranged in a Cartesian array of n columns by m rows respectively; each LED 34 is referenced as $LED_{nm}$ and each photo-diode PD 36 is referenced as $PD_{nm}$.

According to some embodiments the tester unit 2 includes a controller 110. The controller 110 may include a microprocessor 102 which may access a read/write memory 108. Tester unit 2 may connect microprocessor 102 of controller 110 via bidirectional signal lines to multiple LEDs 34 and PDs 36 via multiplexer (MUX)/demultiplexer (DMUX) 106. Microprocessor 102 is able to addressably access, send and/or receive a signal to specific photo-diodes 36 and/or specific light emitting diodes 34 in tester unit 2 by use of MUX/DMUX 106 controlled by microprocessor 102. Microprocessor 102 may receive input signals from multiple PDs 36 through an analogue to digital converter (A/D) 100. Output from microprocessor 102 to multiple LEDs 34 is via a digital-to-analogue converter (D/A) 104. The tester unit 2 may also include a communication module 112, such as a serial interface and/or a wired or wireless communication module configured and operable for connecting controller 110 to an external processing system (such as processing system (processor) 200 described with reference to FIG. 5a, which may be a computerized system adapted to receive and process measured data/signals from the tester unit 2, to determine the condition of the eggs inspected by the tester unit 2.

Figure 7:
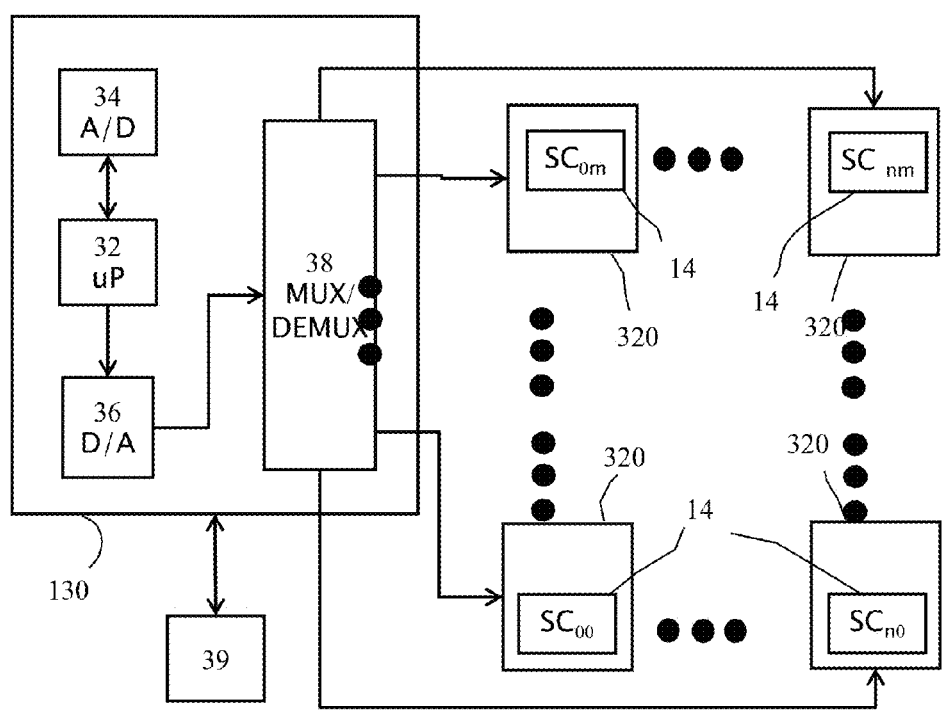
FIG. 7 shows a system block diagram of a removal mechanism used to transfer viable eggs from an incubation tray to a hatching tray, according to a feature of the present invention.

Reference is now made to FIG. 7 which shows a simplified system block diagram for removal mechanism 4 used to transfer eggs 6 from an incubation tray to a hatching tray, according to a feature of the present invention. Removal mechanism 4 may include multiple actuators 320 and multiple suction cups 14. Actuators 320 may operate by selectively allowing or not allowing suction to suction cups 14. Actuators 320 may be arranged in an array of n columns by m rows respectively, each actuator 320 operates a corresponding suction cup 14 with four suction cups 14 shown with locations labeled by $SC_{nm}$. Removal mechanism 4 may connect to control unit 130 via bidirectional signal lines connected to the multiple suction cups 14 via multiplexer (MUX) 38. Microprocessor 32 is able to uniquely access and send a signal to a specific suction cup 14 in removal mechanism 4 by use of MUX 38 controlled by microprocessor 32. Access from microprocessor 32 to multiple suction cups 14 may be performed using multiplexer MUX 38 and digital to analogue converter (D/A) 36. A serial interface 39 may connect to control unit 130 so as to connect an external computer system for the purpose of configuring the operation of control unit 130. Microprocessor 32 may access read/write memory 108 which stores the locations of viable and/or non-viable eggs 6. Moreover, microprocessor 32 and microprocessor 102 may be the same microprocessor.

Figure 8:
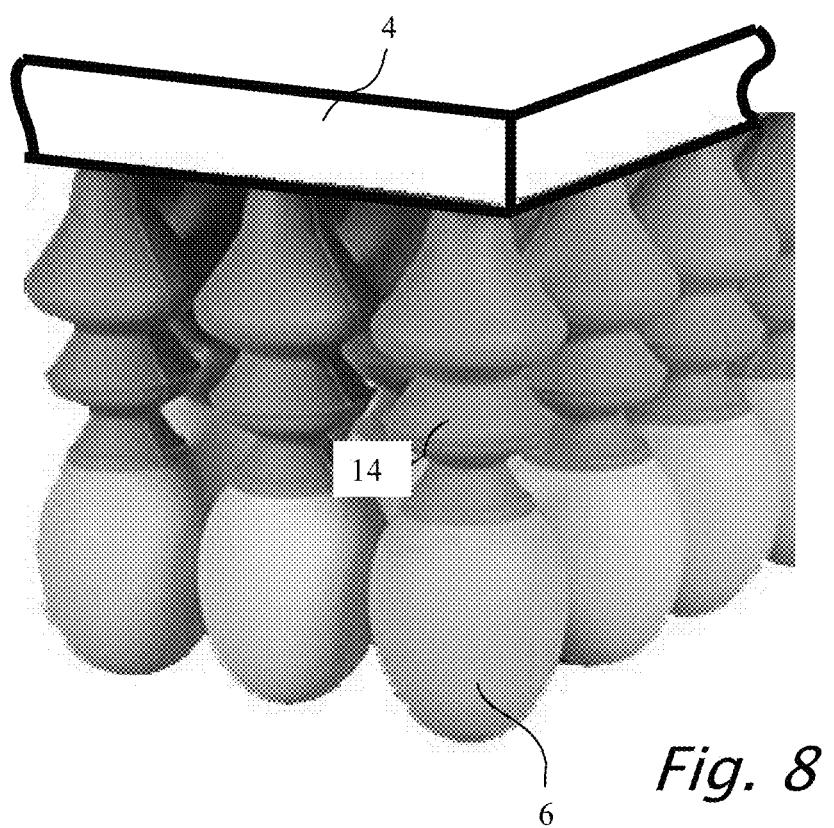
FIG. 8 shows a partial isometric view of the removal mechanism, according to a feature of the present invention.

Reference is now made to FIG. 8 which shows a partial isometric view of removal mechanism 4, according to a feature of the present invention. The partial isometric view shows eggs 6 held by suction cups 14 which may provide a vacuum to hold eggs 6 by suction. Particular eggs 6 may not be held by virtue of the vacuum not being applied to particular suction cups 14.

Figure 9A:
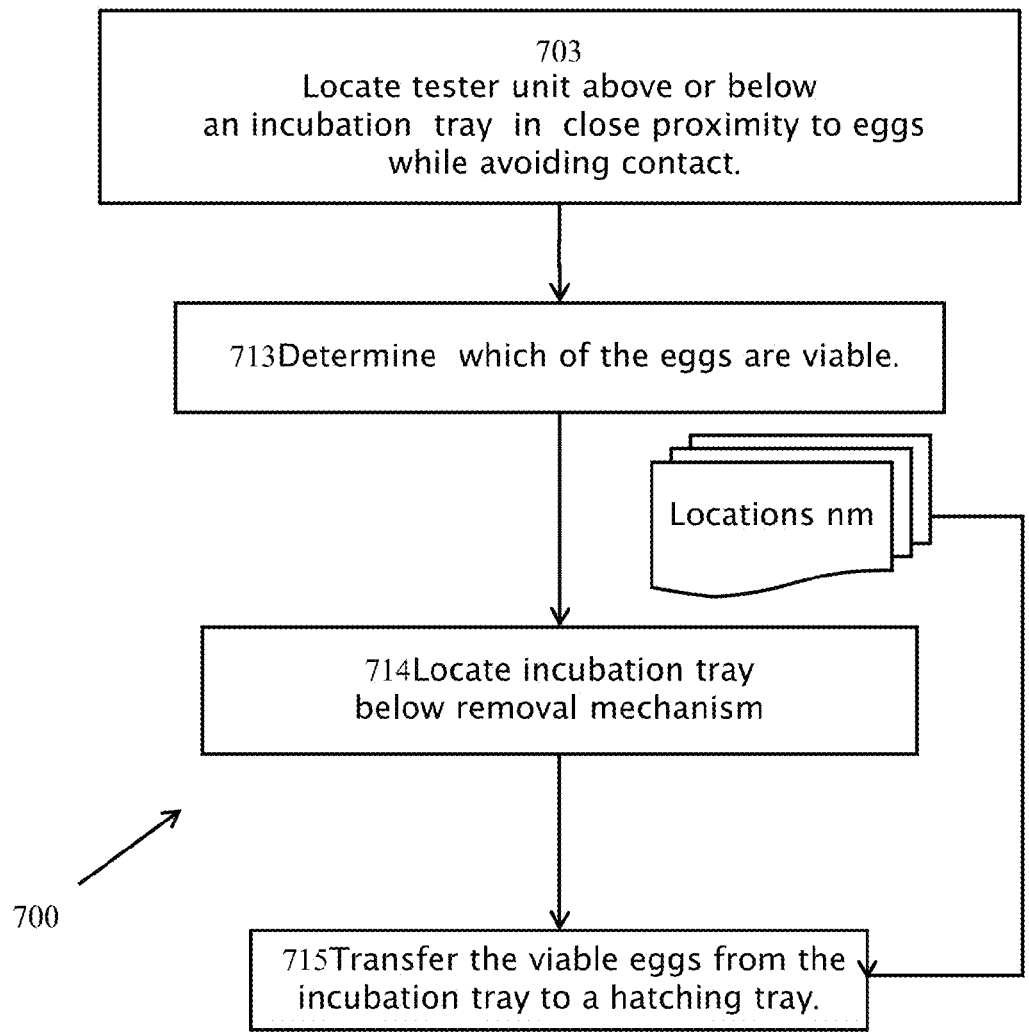
FIG. 9a shows a flow diagram of a method for transferring viable eggs to a hatching tray, according to features of the present invention.
Figure 9B:
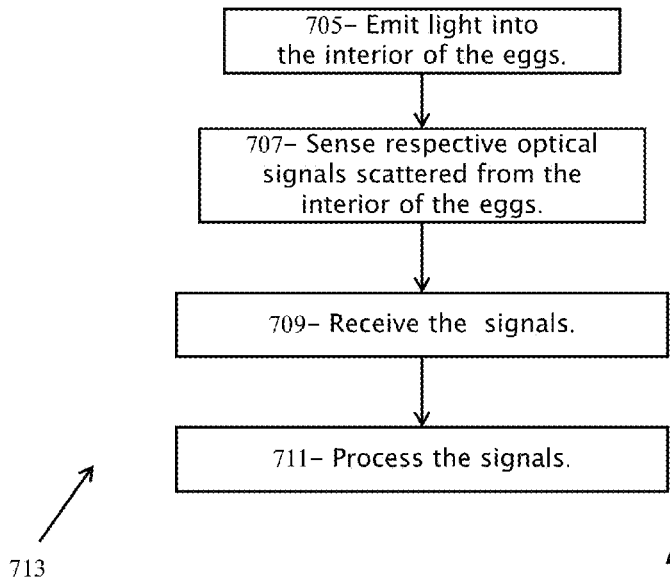
FIG. 9b shows a flow diagram of a portion of the method of FIG. 9a for determination of the viability of an egg.
Figure 9C:
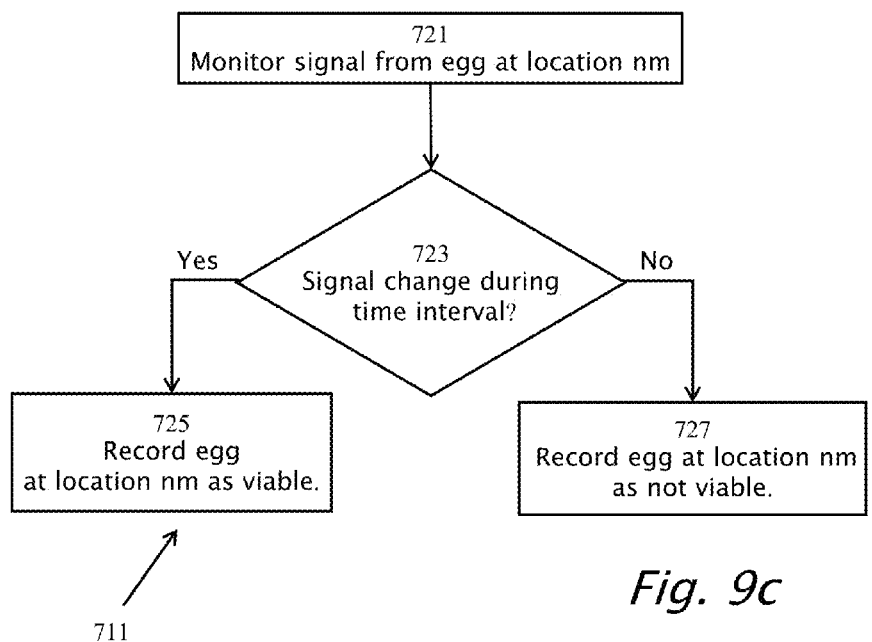
FIG. 9c shows a flow diagram of the processing step in FIG. 9b in greater detail, for determination of viability of an egg, according to different embodiments of the present invention.

Reference is now made to FIGS. 9a, 9b and 9c which illustrate method 700, according to a feature of the present invention. Referring also back to FIG. 2, incubation tray 16 with eggs 6 may be placed on conveyor 8 so that viability test unit 2 is above incubation tray 16 and housings 120 are located (step 703) over eggs 6. Arms 22a and 22b which house photo-diodes PDs 36 and LEDs 34 in each housing 120 respectively are located (as part of step 703) in close proximity to eggs 6 but are not in contact with eggs 6. In step 705 (FIG. 9b), eggs 6 have their interiors illuminated by electromagnetic radiation emitted from respective LEDs 34. Electromagnetic radiation signals scattered from the interior of the eggs (as a result of step 705) are sensed (step 707) by respective photo diodes PDs 36.

In step 709, monitor/control unit 110 receives the sensed electromagnetic radiation signals scattered from the interior of eggs 6. Each of the sensed electromagnetic radiation signals from each egg 6 is then processed by processor 102 (step 711). Based on the processing (step 711), processor 102 determines (step 713) the viability of eggs in incubation tray 16. Locations nm of viable eggs 6 or non-viable eggs are determined and available to removal mechanism 4.

Incubation tray 16 with eggs 6 may be placed on conveyor 8 so that removal mechanism 4 is directly above incubation tray 16 in step 714. In step 715, the viable eggs 6 are removed from incubation tray 16 by removal mechanism 4 and transferred into a hatching tray based on the locations determined in step 713.

According to a feature of the present invention, in order to reduce or eliminate cross-talk between the signals, eggs 6 may be illuminated (step 705, FIG. 9b) and signals are sensed (step 707) during specific time slots so that eggs adjacent to location nm, in locations such as (n−1)m, (n+1)m, n(m−1), n(m+1) are monitored in different time slots.

In order to reduce the effects of ambient noise, ambient noise of photodiode at location nm may be measured during "off" time slots, when the corresponding LED 34 at location nm is not emitting. The noise may be subtracted from the received signal level in software as programmed in processor 102 or a dedicated circuit including a differential amplifier may be used to provide a difference signal between the received signal level and the ambient noise.

Reference is now made to FIG. 9c which shows a flow diagram of step 711 of signal processing, according to feature of the present invention. A signal from egg 6 located at location nm is monitored (step 721). In decision block 723, if a signal change over a threshold is detected during a time interval, then egg 6 at location nm is recorded or tagged in memory 108 as viable (step 725). Otherwise, if there is no signal change for instance during a previously determined time over a threshold, then egg 6 located at nm is determined to be non-viable and the location of the non-viable egg is stored or tagged in memory 108 (step 727).

The signal change in the signals may indicate for instance movement of a live embryo within the viable eggs, a heartbeat of a live embryo in the viable eggs and/or breathing cycles and/or hemoglobin in the viable eggs being oxygenated.

Figure 10:
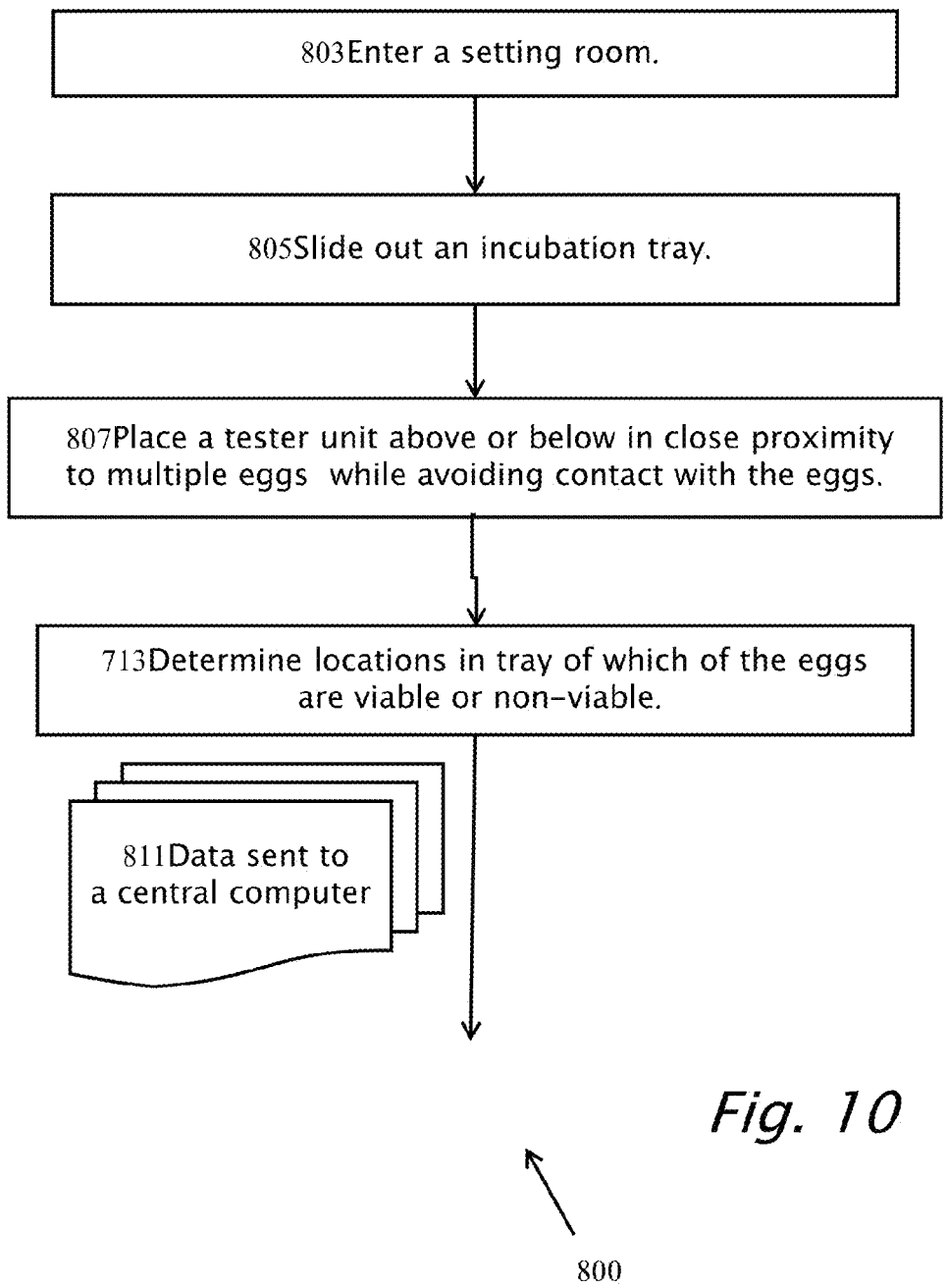
FIG. 10 illustrates a method for determining viability of a sample of eggs in the incubator, according to a feature of the present invention.

Reference is now made to FIG. 10 and again to FIG. 1a. FIG. 10 illustrates method 800, according to a feature of the present invention for testing viability in incubator 60 of eggs for instance between 8 and 12 days of incubation. In step 803, an operator of tester unit 2 enters an incubator 60 with tester unit 2 to determine viability of eggs 6 in incubation tray 16. Tester unit 2 may have an on-board power supply or the operator may use power provided in incubator 60. Incubation tray 16 may be partially or completely slid out (step 805) of incubation trolley 62 on rails 64. Tester unit 2 is then located above eggs 6 of incubation tray 16 (step 807). Step 807 locates arms 22b and arms 22a in close proximity to but not in contact with eggs 6 optionally using pillars on tester unit 2. A test button located on tester 2 may be pressed to test viability (step 713) of eggs 6 in incubation tray 16. An indicator on tester 2 may be used to indicate the end of step 713 to the operator. The operator may optionally leave a tester unit 2 located over eggs 6 so that eggs 6 may be monitored and tested over a number of days if required. The results 811 of step 713 may be relayed by a wireless transceiver located in tester 2 over a local area network (LAN) to a central computer or stored locally in memory 108 of tester 2 for later transfer to the central computer. Multiple applications of method 801 in incubator 60 and/or incubators 60 may be collected by the central computer where statistical analysis may be performed on the results 811 obtained from multiple applications of method 801. In particular, for viability, in incubator 60 between 8 and 12 days of incubation, an analysis of absolute signal level may be performed which indicates which of the non-viable eggs are "clear" eggs which may never have been fertilized and/or which of the non-viable eggs are "black" eggs in which an embryo has died during incubation. The statistical analysis of the non-viable eggs serves to indicate problems with fertilization and/or control issues during incubation.

Advantages of the various embodiments of the present invention as shown in FIGS. 1a and 1b, 3, 10 and 12a and 12b, include:

- Viability tests of eggs 6 without having to move the eggs 6 to and from a separate candling room, where movement of eggs 6 may reduce the viability of eggs 6.
- Viability tests of eggs 6 between 8 to 12 days subsequent to placement of eggs 6 in incubator 60 may provide feedback to suppliers of eggs 6 regarding quality of fertilization, handling and storage processes of eggs 6 prior to incubation.
- Viability tests of eggs 6 between 8 to 12 days subsequent to placement of eggs 6 in incubator 60 provides an advanced indication regarding how many eggs 6 may be viable towards the end of the incubation period.
- Data collected of eggs 6 tested between 8 to 12 days subsequent to placement of eggs 6 in incubator 60 allows a comparison with data for the viability of the same eggs 6 measured prior to selection and transfer of viable eggs 6 to hatching trays. The comparison may provide an evaluation which indicates where viability of eggs 6 may have been lost during the incubation process.

Figure 11:
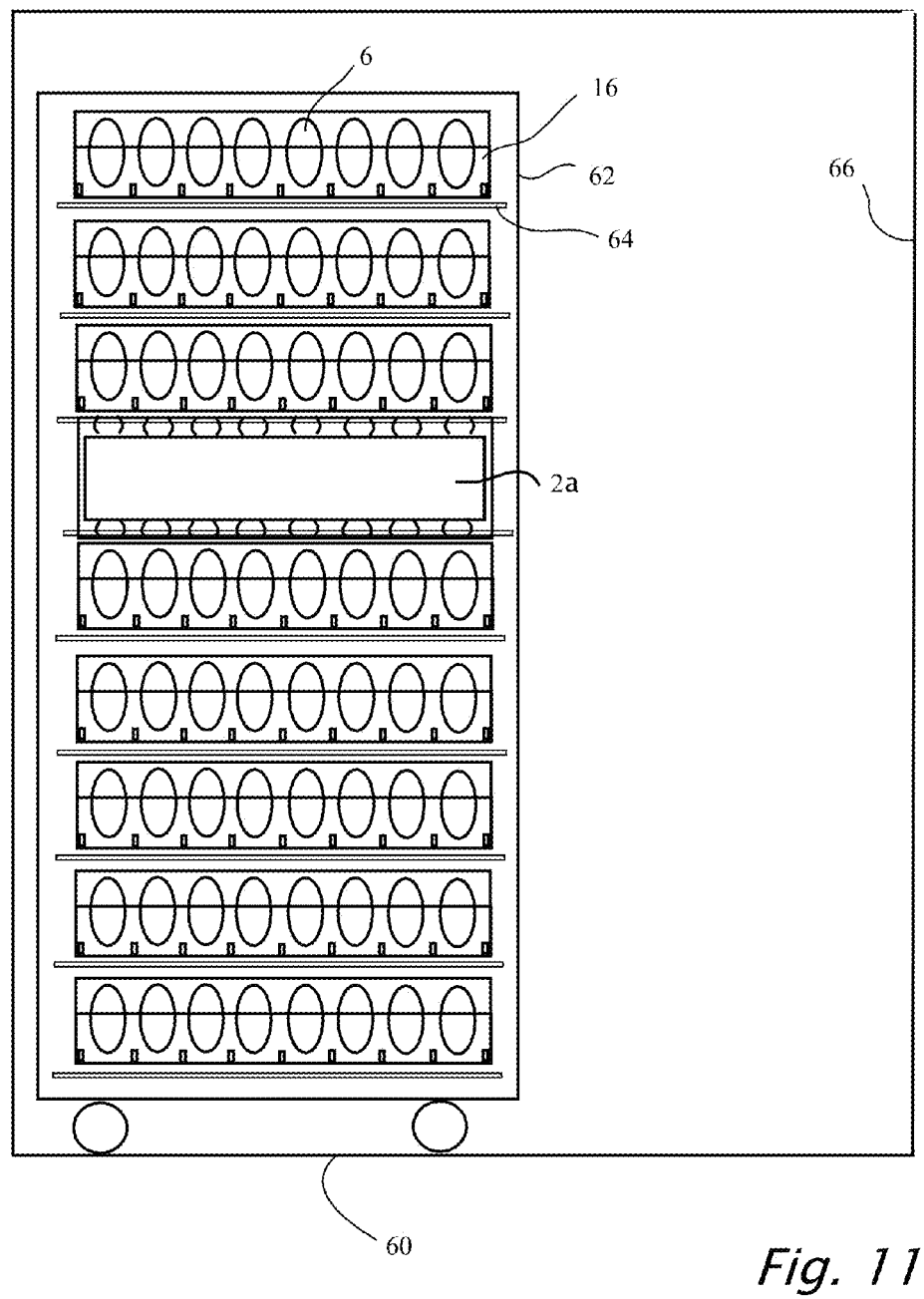
FIG. 11 shows a side view of an incubator, according to a feature of the present invention.

Reference is now made to FIG. 11 which shows a side view of an incubator 60, according to a feature of the present invention. Incubator 60 has entrance door 66 which provides access to incubation trolley 62. A number of incubation trays 16 are shown in situ. One incubation tray 16 is shown removed completely and replaced by viability tester unit 2a such as that illustrated in FIG. 1b, which is configured as a standalone tester unit. In situ, viability tester unit 2a is seen with sub-systems (inspection modules) 31 above eggs 6 in one incubation tray 16 and with sub-systems 31 below eggs 6 in another incubation tray 16. Alternatively, viability tester unit 2a may be formed from two viability tester units 2 placed back-to-back as with viability tester unit 2a, one viability tester unit 2 with sub-systems 31 is seen above eggs 6 in one incubation tray 16 and the other viability tester unit 2 with sub-systems 31 below eggs 6 in another incubation tray 16. Viability tester unit 2a may include and/or may not include filters 35. Viability tester unit 2a may further include a wireless transmitter to a wireless local area network (WLAN), e.g. based on a standard of Institute of Electrical and Electronics Engineers' (IEEE) 802.11, to transmit the viability status of eggs 6 and their locations in incubation tray 16 to a nearby local area network (LAN). Tester unit 2a may include a button (not shown) to initiate a test of multiple eggs and an indicator (LED) (not shown) to initiate and confirm completion of a viability test of eggs 6.

In another alternative feature, instead of leaving testers 2/2a in situ so as not to disturb eggs 6 in incubator 60, testers 2/2a may be moved to different locations in incubator 60 so that possible areas within incubator 60 may be identified which did not provide optimal incubation conditions for eggs 6 located there.

In alternative embodiments, the tester unit 2a may be integrated to be part of an incubation tray 16. In this case the inspection modules 31 of the tester unit 2a may be configured similarly to those shown in FIGS. 4a and 4b and adapted for examining the eggs in the tray 16 from above or below the eggs (along their longitudinal axes) and operating in reflection mode (where both irradiating the egg and detecting the radiation response are performed from generally the same side). Accordingly, the inspection modules 31 may be located in this embodiment at the top or bottom of the incubation tray 16, and may be adapted for monitoring the eggs 6 in the incubation tray 16 from above or below and possibly also monitoring from the bottom the eggs 6 in another incubation tray that is located above tray 16 or monitoring from above the eggs 6 of another incubation tray that is located below tray 16 respectively.

Alternatively or additionally, tester unit 2a may be integrated to be part of an incubation tray 16 and the inspection modules 31 of the tester unit 2a may be configured similarly to those shown in FIGS. 4c and/or 4d. In this case the inspection modules 31 are adapted for examining the eggs in the tray 16 from the sides of the eggs and operating in reflection mode, or transmission mode (where irradiating the egg and detecting the radiation response therefrom are performed from opposite lateral sides of the egg (across their longitudinal axes). Accordingly, in these embodiments the inspection modules 31 may be located in side walls located in between the eggs (e.g. between the rows of eggs in the tray). This configuration of an incubation tray 16 integrated with the tester unit 2a is described in more detail in the following with reference to FIGS. 12a and 12b.

Figure 12A:
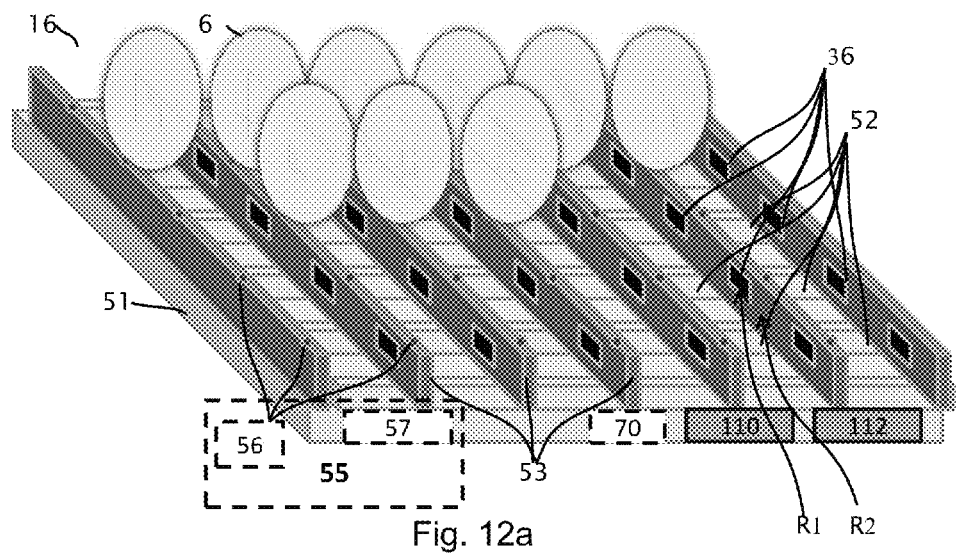
FIGS. 12a and 12b are two perspective views showing an incubation tray according to an embodiment of the present invention integrated with a tester unit of the present invention.
Figure 12B:
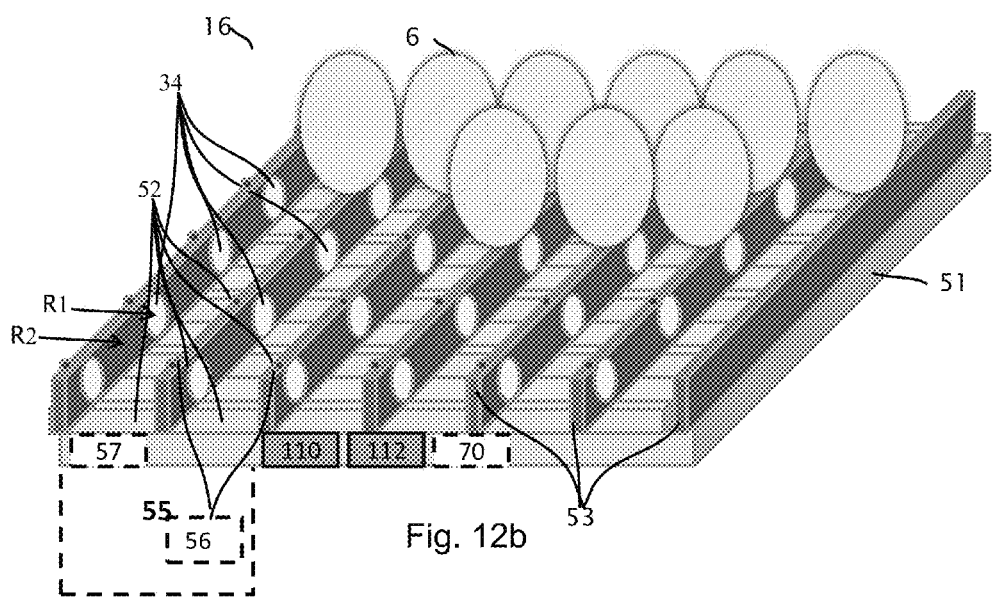

FIGS. 12a and 12b show two perspective views, from opposite angles, of an incubation tray 16 for use within an egg incubator according to an embodiment of the present invention. The incubation tray 16 is adapted for placement within an egg incubator and includes an enclosure 51 defining a plurality of egg placements 52 for carrying a plurality of eggs 6 for incubation within an egg incubator. The incubation tray 16 integrated with a tester unit includes a controller 53 and a plurality of inspection modules 31 located in the vicinity of the egg placements 52 and which are connectable to the controller 110. The inspection modules 31 are configured and operable for inspecting the eggs 6 in the incubation tray 16, possibly in situ, while the incubation tray 16 is within an eggs incubator, to provide measured data indicative of radiation response from the eggs. Accordingly the controller includes, or is associated with a communication module 112, which is configured to communicate the measured data to processing system (not shown) possibly located outside the incubator.

The controller 110 may be for example configured as described above with reference to FIG. 6.

The inspection modules 31 may be for example configured as described above with reference to any one of FIGS. 4c and 4d and adapted for inspecting the eggs 6 from their lateral side, by operating either in reflection or in transmission modes. To this end each of the inspection modules 31 includes at least one electromagnetic radiation emitter 34 and at least one sensor 36 of electromagnetic radiation returning from the egg 6 (possibly more than one). The electromagnetic radiation emitter 34 and at least one sensor 36, are configured and operable for respectively inspecting the plurality of eggs 6 located in the egg placements 52, by irradiating the eggs with electromagnetic radiation from a lateral side of the eggs and measuring, from a lateral side of the egg, the radiation response returning from the egg.

The controller 110 is connected to the electromagnetic radiation emitter 34 and operates electromagnetic radiation to the eggs 6. The controller 110 is connected to the sensors 36 and configured and operable to obtain therefrom signals indicative of the radiation response from the eggs 6 located in the egg placements 52. The controller 110 stores measured data indicative of the signals received from the sensors 34. The measured data is indicative of the conditions of the eggs in the egg placements 52 and is further processed to determine the conditions/viabilities of the eggs, by an external processing system, such as the processing system 200 described above with reference to FIG. 5a. To this end the controller 110 is configured and operable to communicate the stored measured data to an external processing system, by utilizing the communication module 112.

It is noted that in some embodiments the communication module 112 is a wireless communication module, such as WIFI or Bluetooth module, enabling to wirelessly communicate the measured data from within the incubator to the external processing system outside the incubator.

In some embodiments, in order to reduce/prevent cross talk between the inspection of neighboring eggs, controller 110 is configured to operate inspection modules 31 of neighboring egg placements, at different (e.g. non-overlapping) time intervals. This may be achieved by operating the emitters 34 of the neighboring egg placements at different time intervals, and/or by recording the signals obtained from the sensors 36 of the neighboring egg placements at the different time intervals.

In some embodiments the emitter 34 of an inspection module 31 is configured and operable for emitting optical radiation within a certain wavelength range (e.g. in the Near IR regime 600-1000 nanometers wavelength) to illuminate an egg located in the respective egg placement. The sensor 36 of the inspection module 31 is adapted to detect the optical radiation in that wavelengths range that is scattered in response to illumination from within the respective egg in the egg placement.

In some embodiments the emitter 34 and the sensor 36 of an inspection module 31 in the incubation tray 16 are located at substantially opposite lateral sides of the egg placement 52 associated with the inspection module 31. Accordingly the inspection module is configured and operable in transmission mode, which advantageously allows measuring both the dynamic and the static parameters of the radiation response from the egg with good accuracy. Also the inspection module operates to inspect the eggs from the lateral sides thereof, thereby proving simple design of the incubation tray 16 which facilitates: (i) convenient handling (placement/removal) of eggs from the tray 16; (ii) compatibility with conventional/existing egg incubators (since the tray's height may be in accordance with the standard); (iii) measurement of the radiation response through the lateral side of the egg which requires lower radiation intensity as compared to measurement of the transmission along the longer longitudinal axis of the egg.

According to some embodiments of the present invention the incubation tray 16 is configured/structured such that it has side walls/panels 53 extending laterally and horizontally along the incubation tray, and defining locations of the egg placements 52 in between them. The emitter 34 and sensor 36 of the inspection modules 31 of respective egg placements 51 are located at the side walls 53, such that emission and detection of the radiation to and from the egg 6 in the egg placement 52 is performed laterally across the egg 6.

Optionally as illustrated in FIGS. 12a and 12b the emitter 34 and sensor 36 of each inspection module 31 are located from opposite sides of the respective egg placement 52, such that the inspection module 31 is configured to operate in transmission mode.

Alternatively, the emitter 34 and the sensor 36 are placed at a side wall/panel 53, from the same side of the egg placement 52 associated therewith. Accordingly the inspection module is configured for operation in reflection mode. In this case the emitter 34 and the sensor 36 are arranged such that illumination and detection axes/paths thereof are tilted (e.g. with tilt angle θ within the range of 50 to 120 degrees) with respect to one another, to prevent/suppress detection of radiation reflected from a shell of an egg 6 located in the egg placement 52.

In some embodiments the emitter 34 and sensor 36 are accommodated within the side walls (e.g. at voids therein). The enclosure 51, or at least the side walls/panels 53 thereof are configured to be sealed to water and/or other contaminants/dirt, to protect and facilitate robust and reliable operation of the inspection modules 31. The walls are configured to be transmissive to the wavelength range used for irradiating the egg and detecting the radiation response from the eggs. In some cases the walls are configured to function as spectral filters transferring radiation at that wavelength range and blocking transmittance of radiation of other wavelength ranges therethrough (e.g. the walls may be made/coated by material compositions providing such spectral filtration).

To this end, in some embodiments the walls are configured to prevent or at least reduce cross talk between the inspections of neighboring cells. For instance, in some implementations a region R1 of the wall 51 located between the emitter and/or sensor of the inspection module 31 and the designated location of the egg 6 in the respective egg placement 52, is configured to be transparent to enable uninterrupted radiation propagation between the emitter/sensor and the location of the egg 6, and possibly permit focusing of the radiation on the egg 6. Regions R2 of the walls surrounding the region R1 associated with the emitter and/or the sensor (e.g. regions R2) are located across a line of site between the emitter/sensor of the inspection module 31 and other egg placements 52, not associated with that particular inspection module 31 may be configured to be translucent/diffusive and/or opaque to the spectral range used for the inspection in order to prevent cross talk of the inspecting radiation and/or the radiation response in between different egg placements 52.

In some implementations the emitter 34 includes, or is associated with, focusing optics (not specifically shown) located in an optical path between the emitter 34 and a designated location of the egg 6 in the egg placement 52. The focusing optics are configured for focusing the radiation used for inspection on the egg 6, and may include one or more lenses coupled to the emitter 34 and/or a lens formed in the region R1 of the walls 53 between the emitter 34 and the designated location of the egg.

In some embodiments the incubation tray defines a two dimensional arrangement of plurality of egg placements 52. The side walls/panels extend alone on one lateral direction of the incubation tray 16, only in between rows of egg placements 52 in the tray 16 (but not between egg placements in the same row). Accordingly, such an arrangement of the side walls/panels facilitates/permits relatively free flow of air in between the eggs in the tray 16 along the direction of the walls 53 for ventilating the eggs during incubation.

Also shown is an optional flagging system 55 integrated with the incubation tray. The flagging system 55 includes a plurality of indicators 56 (e.g. implemented in this example by LED emitting visible light) associated respectively with the designated locations (egg placements) of the eggs in the tray 16 and located adjacent thereto. The flagging system 55 also includes a flagging control system 57 connected to the indicators 56 and adapted to control their operation. The flagging control system 57, which may be implemented as an analogue and/or digital circuitry, is associated with a communication module (not specifically shown, and is adapted to communicate with the processor to receive therefrom the location of the viable/non-viable eggs in the tray 16. The flagging control system 57 operates the indicators 56 in accordance with the locations of the viable/non-viable eggs in the tray 16, for example by lighting the LEDs of non-viable eggs. In some embodiments the flagging control system 57, may be part of the controller 110 or as a separate module.

As illustrated in FIGS. 12a and 12b, optionally, the incubation tray 16 according to some embodiments of the invention is also configured and operable for monitoring the turning (rolling and/or tilting) of the eggs therein during the incubation period. The incubation tray 16 may include includes a tilt/roll sensor(s) 70 (e.g. accelerometer and/or a gyro sensor(s), which may be for example a part of the tester unit 2) that is configured and operable to measure the degree of tilt and/or the roll rate of the eggs in the tray 16 during the incubation. The tilt/roll sensor(s) 70 may be implemented in (e.g. located on/within and possibly integrated with) the incubation tray 16 and may be connected to the controller 110. The controller 110 receives from the tilt/roll sensor(s) 70 measured tilt data indicative of the eggs tilting, and/or turning/rolling rate(s), during periods of the incubation is capable of providing/using that data for further processing by which the quality of the incubation conditions can be determined, and possibly the operation of the incubator is controlled/adjusted.

Figure 12C:
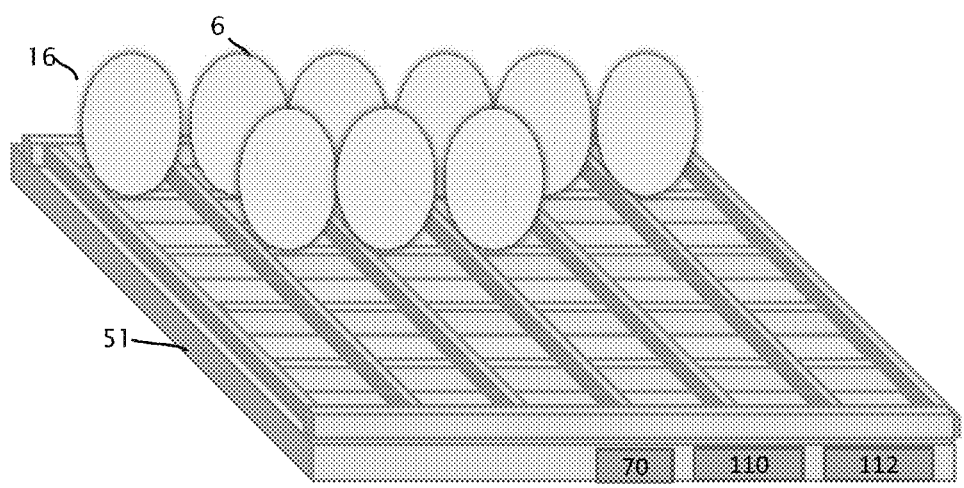
FIG. 12c is a perspective view of an incubation tray including tilt sensor according to an embodiment of the present invention.

FIG. 12c is an incubation tray 16 according to another embodiment of the present invention including tilt/roll sensor(s) 70, as described above with reference to FIGS. 12a and 12b, embedded in the incubation tray 16 and a controller and 110 connectable to the tilt/roll sensor(s) 70, for receiving measured tilt data therefrom, and communication module 112, connectable to the controller 110 and adapted for communication the measured tilt data for further processing by a processing unit by which the incubation conditions can be assessed based on at least the measured tilt data.

The indefinite articles "a", "an" as used herein, such as "an incubation tray", "a multiplexer" have the meaning of "one or more" that is "one or more incubation trays", or "one or more multiplexers".

Although selected features of the present invention have been shown and described, it is to be understood the present invention is not limited to the described features. Instead, it is to be appreciated that changes may be made to these features without departing from the principles and spirit of the invention, the scope of which is defined by the claims and the equivalents thereof.

The invention claimed is:

1. An incubation tray for use within an egg incubator,
   the incubation tray is adapted for placement within an egg incubator and comprises an enclosure defining a plurality of egg placements for carrying a plurality of eggs for incubation within an egg incubator, wherein said enclosure includes one or more walls extending laterally along said incubation tray, and defining locations of said egg placements in between them;
   the incubation tray comprises a tester unit comprising a plurality of inspection modules located by said enclosure and associated with the plurality of egg placements respectively; the inspection modules each include at least one radiation emitter and at least one sensor, and are configured and operable for respectively inspecting the plurality of eggs located in the egg placements, by irradiating the eggs with radiation from a lateral side of the eggs and measuring a response from a lateral side thereof to determine measured data indicative of conditions of the eggs in the egg placements, wherein said emitter and sensor are located within or behind said one or more walls, and wherein said one or more walls are transmissive to a wavelength range of said radiation along a propagation path between said respective egg placement and said emitter and sensor;

the incubation tray comprises a communication module configured and operable for receiving said measured data from the tester unit and communicating said data to a processing system to enable determining data indicative of condition of the eggs in the incubation tray based on said measured data;

wherein said one or more walls are configured in one or more of the following configurations:

(i) said one or more walls are configured to be transparent to said radiation at regions intersecting the propagation path in between said emitter and a designated location of an egg in an egg placement corresponding to said emitter, and said one or more walls are configured to be substantially opaque or diffusive to said radiation at regions intersecting a line of sight of said emitter with neighboring egg placements not associated with said emitter;

(ii) said one or more walls are configured to be transparent to said radiation at regions intersecting the propagation path in between said sensor and a designated location of an egg in an egg placement corresponding to said sensor, and said one or more walls are configured to be substantially opaque or diffusive to said radiation at regions intersecting a line of sight of said sensor with neighboring egg placements not associated with said sensor;

thereby reducing crosstalk between inspection of eggs in neighboring egg placements in said tray.

2. The incubation tray of claim 1 wherein said communication module is configured as a wireless communication module and is adapted for wireless communication with said processing system thereby enabling inspecting the plurality of eggs in said incubation tray and communication of said measured data while said incubation tray is within an incubator.

3. The incubation tray of claim 1 wherein said condition of the eggs is indicative of at least one of the following: condition of embryos within said eggs and condition of shells of said eggs.

4. The incubation tray of claim 1 wherein said emitter and said sensor are configured and operable to emit and detect electromagnetic radiation.

5. The incubation tray of claim 4 wherein said emitter and said sensor are configured and operable to emit and detect radiation at a certain optical wavelengths range.

6. The incubation tray of claim 5 wherein said certain wavelength range is in the Near-IR wavelength range from 600 to 1000 nanometers.

7. The incubation tray of claim 1 wherein said tester unit comprises a controller configured and operable for processing signals from said sensor to obtain said measured data and storing said measured data to enable communication of said measured data to said processing system.

8. The incubation tray of claim 1 wherein said emitter and said sensor are located with respect to said egg placement such that irradiation of the egg and detection of the radiation response from the egg are performed laterally from opposite lateral sides of the egg, thereby providing said measured data which is indicative of transmittance through the egg associated with a size of an embryo therewithin.

9. An incubation tray for use within an egg incubator, wherein the incubation tray is adapted for placement within an egg incubator and comprises an enclosure defining a plurality of egg placements for carrying a plurality of eggs for incubation within an egg incubator, the incubation tray comprises a tester unit comprising a plurality of inspection modules located by said enclosure and associated with the plurality of egg placements respectively; the inspection modules each include at least one radiation emitter and at least one sensor, and are configured and operable for respectively inspecting the plurality of eggs located in the egg placements, by irradiating the eggs with radiation from a lateral side of the eggs and measuring a response from a lateral side thereof to determine measured data indicative of conditions of the eggs in the egg placements, the incubation tray comprises a communication module configured and operable for receiving said measured data from the tester unit and communicating said data to a processing system to enable determining data indicative of condition of the eggs in the incubation tray based on said measured data, said inspection modules are located within the enclosure and the enclosure is configured to be watertight.

10. The incubation tray of claim 9, wherein said enclosure includes one or more walls extending laterally along said incubation tray, and defining locations of said egg placements in between them, and wherein said emitter and sensor are located at said walls.

11. The incubation tray of claim 10 wherein said emitter and sensor are located within or behind said one or more walls, and wherein said one or more walls are transmissive to a wavelength range of said radiation along a propagation path between said respective egg placement and said emitter and sensor.

12. The incubation tray of claim 11 wherein said one or more walls are configured in one or more of the following configurations:

said one or more walls are configured to be transparent to said radiation at regions intersecting the propagation path in between said emitter and a designated location of an egg in an egg placement corresponding to said emitter, and said one or more walls are configured to be substantially opaque or diffusive to said radiation at regions intersecting a line of sight of said emitter with neighboring egg placements not associated with said emitter;

said one or more walls are configured to be transparent to said radiation at regions intersecting the propagation path in between said sensor and a designated location of an egg in an egg placement corresponding to said sensor, and said one or more walls are configured to be substantially opaque or diffusive to said radiation at regions intersecting a line of sight of said sensor with neighboring egg placements not associated with said sensor;

thereby reducing crosstalk between inspection of eggs in neighboring egg placements in said tray.

13. The incubation tray of claim 10 wherein at least a region of said one or more walls is configured and operable as a spectral filter for passing radiation in said certain wavelength range and preventing passage of radiation of other wavelength ranges to the sensor.

14. The incubation tray of claim 10 wherein said enclosure is configured to define a two dimensional arrangement of a plurality of egg placements on an upper facet thereof, and wherein said one or more walls are substantially generally aligned along one direction of said two dimensional arrangement to enable free air flow along said direction for ventilating eggs located in the egg placements.

15. The incubation tray of claim 10 wherein said inspection modules are configured to inspect an egg in said egg placement from its lateral side by operating in transmission mode and said emitter and sensor are respectively placed at said walls from the opposite sides of the egg placement.

16. The incubation tray of claim 10 wherein said inspection modules are configured to inspect an egg in said egg placement from its lateral side by operating in reflection mode and said emitter and sensor are placed at said one or more walls from the same side of the egg placement.

17. The incubation tray of claim 16 wherein said emitter and sensor are arranged such that illumination and detection paths defined thereby are tilted with respect to one another, to thereby prevent/suppress detection of radiation emitted from said emitter and reflect from a shell of an egg located in the egg placement.

18. The incubation tray of claim 1 wherein said tester unit comprises a controller adapted for operating inspection modules of neighboring egg placements at different substantially non overlapping time intervals to thereby reduce cross talk between the inspections of eggs in the neighboring egg placements.

19. The incubation tray of claim 1 wherein said tester unit comprises a controller adapted for operating inspection modules for inspecting eggs in said egg placement for a duration of at least few seconds such that said measured data, obtained in said duration, is indicative of dynamic parameters of the radiation response from said eggs, enabling determination of physiological development stage of embryos within said eggs.

20. The incubation tray of claim 1 wherein said tester unit comprises at least one tilt sensor capable of measuring tilting of eggs in said tray during incubation, and wherein said controller is connectable to the tilt sensor, and adapted for receiving therefrom measured tilt data indicative of said tilting and communicating said measured tilt data for further processing to enable determining data indicative of incubation condition applied to said eggs.

21. An incubator comprising the incubator tray of claim 1, and the processing system for processing the measured data of radiation response from an egg, the processing system comprising:
 a communication module for obtaining measured data indicative of radiation response obtained by irradiating an egg for a duration of at least a few seconds and detecting the radiation scattered from said egg at said duration;
 a dynamic parameter analyzer adapted to process the measured data to determine dynamic parameters indicative of periodical variations in the intensity of the radiation response from the egg and utilize said dynamic parameters to estimate physiological development stage of an embryo within said egg;
 a static parameter analyzer adapted to process the measured data to determine static parameters indicative of a magnitude of the radiation response from the egg and utilize said static parameters to estimate growth of said embryo within said egg; and
 an embryo condition estimator configured to determine a condition of said embryo based on said estimated growth and said physiological development stage of said embryo.

22. The incubation tray of claim 1 wherein at least a region of said one or more walls is configured and operable as a spectral filter for passing radiation in said certain wavelength range and preventing passage of radiation of other wavelength ranges to the sensor.

23. The incubation tray of claim 1 wherein said enclosure is configured to define a two dimensional arrangement of a plurality of egg placements on an upper facet thereof, and wherein said one or more walls are substantially generally aligned along one direction of said two dimensional arrangement to enable free air flow along said direction for ventilating eggs located in the egg placements.

24. The incubation tray of claim 1 wherein said inspection modules are configured to inspect an egg in said egg placement from its lateral side by operating in transmission mode and said emitter and sensor are respectively placed at said walls from the opposite sides of the egg placement.

25. The incubation tray of claim 1 wherein said inspection modules are configured to inspect an egg in said egg placement from its lateral side by operating in reflection mode and said emitter and sensor are placed at said one or more walls from the same side of the egg placement.

26. The incubation tray of claim 25 wherein said emitter and sensor are arranged such that illumination and detection paths defined thereby are tilted with respect to one another, to thereby prevent/suppress detection of radiation emitted from said emitter and reflect from a shell of an egg located in the egg placement.

27. An incubator comprising the incubator tray of claim 9, and the processing system for processing the measured data of radiation response from an egg, the processing system comprising:
 a communication module for obtaining measured data indicative of radiation response obtained by irradiating an egg for a duration of at least a few seconds and detecting the radiation scattered from said egg at said duration;
 a dynamic parameter analyzer adapted to process the measured data to determine dynamic parameters indicative of periodical variations in the intensity of the radiation response from the egg and utilize said dynamic parameters to estimate physiological development stage of an embryo within said egg;
 a static parameter analyzer adapted to process the measured data to determine static parameters indicative of a magnitude of the radiation response from the egg and utilize said static parameters to estimate growth of said embryo within said egg; and
 an embryo condition estimator configured to determine a condition of said embryo based on said estimated growth and said physiological development stage of said embryo.

* * * * *